(12) United States Patent
Maroney et al.

(10) Patent No.: US 7,527,631 B2
(45) Date of Patent: *May 5, 2009

(54) ARTHROPLASTY SIZING GAUGE

(75) Inventors: Brian J. Maroney, Fort Wayne, IN (US); Jack F. Long, Warsaw, IN (US); Joseph P. Iannotti, Solon, OH (US); Gerald R. Williams, Jr., Villanova, PA (US)

(73) Assignee: Depuy Products, Inc., Warsaw, IN (US)

( * ) Notice: Subject to any disclaimer, the term of this patent is extended or adjusted under 35 U.S.C. 154(b) by 552 days.

This patent is subject to a terminal disclaimer.

(21) Appl. No.: 10/403,707

(22) Filed: Mar. 31, 2003

(65) Prior Publication Data
US 2004/0193175 A1   Sep. 30, 2004

(51) Int. Cl.
*A61B 17/58* (2006.01)
*A61B 17/60* (2006.01)
*A61F 2/00* (2006.01)

(52) U.S. Cl. .................................. 606/102

(58) Field of Classification Search .......... 606/53, 606/86, 102; 33/501, 511, 512
See application file for complete search history.

(56) References Cited

U.S. PATENT DOCUMENTS

| | | | |
|---|---|---|---|
| 788,362 A * | 4/1905 | Lavery | 33/512 |
| 1,023,542 A * | 4/1912 | Winter | 33/512 |
| 1,345,443 A | 7/1920 | Hood | |
| 1,669,701 A | 5/1928 | Estwing | |
| 2,222,517 A | 11/1940 | Price | |
| 2,243,718 A | 5/1941 | Moreira | |
| 2,718,228 A | 9/1955 | Steembriggje | |
| 2,725,878 A | 12/1955 | Reiter | |
| 3,605,527 A | 9/1971 | Gambale | |
| 3,702,611 A | 11/1972 | Fishbein | |
| 3,840,904 A | 10/1974 | Tronzo | |
| 3,855,638 A | 12/1974 | Pilliar | |
| 3,979,778 A | 9/1976 | Stroot | |
| 4,042,980 A | 8/1977 | Swanson et al. | |
| 4,206,517 A | 6/1980 | Pappas et al. | |
| 4,271,849 A | 6/1981 | Rehder | |
| 4,328,593 A | 5/1982 | Sutter | |

(Continued)

FOREIGN PATENT DOCUMENTS

DE   2041929   8/1970

(Continued)

OTHER PUBLICATIONS

Biomet Orthopedics, Inc., Introducing the Copeland Humeral Resurfacing Head, 2001.

(Continued)

*Primary Examiner*—Anu Ramana

(57) ABSTRACT

A gauge (10) for measuring bone contour (12) of a bone (4) for use in joint arthroplasty is provided. The gauge (10) includes a body (14) and a probe (16). The body (14) has a body contact portion of the body (14) for contact with the bone (4). The probe (16) is movably positional with respect to the body (14). The probe (16) includes a probe contact portion of the probe (16) for contact with the bone (4). The relative position of the probe (16) with respect to the body (14) is indicative of the bone contour (12) of the bone (4).

14 Claims, 25 Drawing Sheets

U.S. PATENT DOCUMENTS

| | | | |
|---|---|---|---|
| 4,332,036 A | 6/1982 | Sutter | |
| 4,355,429 A | 10/1982 | Mittelmeier et al. | |
| 4,550,450 A | 11/1985 | Kinnett | |
| 4,601,289 A | 7/1986 | Chiarizzio et al. | |
| 4,722,330 A * | 2/1988 | Russell et al. | 606/88 |
| 4,752,296 A | 6/1988 | Buechel et al. | |
| 4,846,841 A | 7/1989 | Oh | |
| 4,865,605 A | 9/1989 | Dines et al. | |
| 4,919,669 A | 4/1990 | Lannelongue | |
| 4,987,904 A * | 1/1991 | Wilson | 600/587 |
| 5,064,427 A | 11/1991 | Burkinshaw | |
| 5,070,623 A * | 12/1991 | Barnes | 33/807 |
| 5,116,339 A | 5/1992 | Glock | |
| 5,226,915 A | 7/1993 | Bertin | |
| 5,258,033 A | 11/1993 | Lawes | |
| 5,282,865 A | 2/1994 | Dong | |
| 5,358,525 A | 10/1994 | Fox et al. | |
| 5,423,827 A * | 6/1995 | Mumme et al. | 606/96 |
| 5,454,816 A * | 10/1995 | Ashby | 606/88 |
| 5,470,336 A | 11/1995 | Ling et al. | |
| 5,476,467 A | 12/1995 | Benoist | |
| 5,486,178 A * | 1/1996 | Hodge | 606/82 |
| 5,490,852 A | 2/1996 | Azer | |
| 5,507,817 A | 4/1996 | Craig et al. | |
| 5,540,696 A * | 7/1996 | Booth et al. | 606/88 |
| 5,549,704 A | 8/1996 | Sutter | |
| 5,569,263 A * | 10/1996 | Hein | 606/102 |
| 5,662,476 A | 9/1997 | Ingber et al. | |
| 5,683,395 A | 11/1997 | Mikhail | |
| 5,690,636 A | 11/1997 | Wildgoose | |
| 5,702,460 A | 12/1997 | Carls | |
| 5,723,018 A | 3/1998 | Cyprien et al. | |
| 5,776,194 A | 7/1998 | Mikol et al. | |
| 5,779,710 A * | 7/1998 | Matsen, III | 606/102 |
| 5,800,437 A | 9/1998 | Gustilo et al. | |
| 5,800,557 A | 9/1998 | Elhami | |
| 5,830,216 A * | 11/1998 | Insall et al. | 606/88 |
| 5,957,926 A | 9/1999 | Masini | |
| 6,013,104 A | 1/2000 | Kampner | |
| 6,045,582 A | 4/2000 | Prybyla | |
| 6,102,916 A | 8/2000 | Masini | |
| 6,110,200 A * | 8/2000 | Hinnenkamp | 623/2.11 |
| 6,127,596 A | 10/2000 | Brown et al. | |
| 6,156,069 A | 12/2000 | Amstutz | |
| 6,168,628 B1 | 1/2001 | Huebner | |
| 6,187,012 B1 | 2/2001 | Masini | |
| 6,200,319 B1 | 3/2001 | Storer | |
| 6,206,884 B1 | 3/2001 | Masini | |
| 6,283,999 B1 | 9/2001 | Rockwood, Jr. | |
| 6,319,104 B1 | 11/2001 | Emter | |
| 6,334,874 B1 | 1/2002 | Tornier et al. | |
| 6,364,910 B1 | 4/2002 | Shultz et al. | |
| 6,368,353 B1 | 4/2002 | Arcand | |
| 6,554,865 B2 | 4/2003 | Grusin et al. | |
| 6,709,439 B2 | 3/2004 | Rogers | |
| 6,740,120 B1 | 5/2004 | Grimes | |
| 6,755,865 B2 | 6/2004 | Tarabishy | |
| 6,783,549 B1 | 8/2004 | Stone | |
| 6,942,699 B2 | 9/2005 | Stone | |
| 6,979,299 B2 * | 12/2005 | Peabody et al. | 600/587 |
| 2001/0009971 A1 | 7/2001 | Sherts | |
| 2001/0037152 A1 | 11/2001 | Rockwood | |
| 2002/0016634 A1 | 2/2002 | Maroney et al. | |
| 2002/0183849 A1 | 2/2002 | Grusin et al. | |
| 2002/0099381 A1 | 7/2002 | Maroney et al. | |
| 2002/0099445 A1 | 7/2002 | Maroney et al. | |
| 2003/0114859 A1 | 6/2003 | Grusin et al. | |
| 2003/0163202 A1 | 8/2003 | Lakin | |
| 2005/0065612 A1 | 3/2005 | Winslow | |

FOREIGN PATENT DOCUMENTS

| | | |
|---|---|---|
| DE | 4228710 A1 | 8/1992 |
| DE | 4220217 C2 | 2/1995 |
| DE | 10233204 A1 | 7/2002 |
| EP | 0845250 A2 | 11/1997 |
| EP | 0888752 A2 | 7/1998 |
| EP | 0903128 A1 | 9/1998 |
| EP | 1064890 A1 | 6/2000 |
| EP | 1228739 A2 | 8/2002 |
| FR | 2418664 | 3/1978 |
| FR | 2578739 A1 | 9/1986 |
| FR | 2737107 A1 | 7/1995 |
| GB | 764600 | 4/1955 |
| GB | 2259253 A | 8/1992 |
| WO | WO 94/15551 | 7/1994 |
| WO | WO 95/22302 | 8/1995 |
| WO | WO 98/07393 | 2/1998 |
| WO | WO 99/37254 | 7/1999 |
| WO | WO 01/13823 A2 | 3/2000 |
| WO | WO 01/13823 A3 | 3/2001 |
| WO | WO 02/17822 A1 | 3/2002 |

OTHER PUBLICATIONS

Biomet Merck, LTD., Copeland Surface Replacement Shoulder Arthroplasty, (date unknown).

Endotec, INC. Buechel-Pappas Resurfacing Shoulder System Surgical Procedure by Frederick F. Buechel, M.D. 2001.

Biomet Orthopedics, Inc., Copeland Humeral Resurfacing Head (date unknown).

European Search Report For European Application No. 04251871. 2-1526, Sep. 8, 2004, 3 pages.

European Search Report For European Application No. 05251328. 0-2310, Jul. 21, 2005, 4 pages.

* cited by examiner ns
ARTHROPLASTY SIZING GAUGE

CROSS-REFERENCE TO RELATED APPLICATIONS

Cross reference is made to the following applications: DEP 756 entitled "ARTICULATING SURFACE REPLACEMENT PROSTHESIS", DEP 789 entitled "MODULAR ARTICULATING SURFACE REPLACEMENT PROSTHESIS", DEP 5041 entitled "ARTHROPLASTY INSTRUMENT AND ASSOCIATED METHOD", DEP 5042 entitled "EXTENDED ARTICULATION ORTHOPAEDIC IMPLANT AND ASSOCIATED METHOD" and DEP 5052 entitled "PROSTHETIC IMPLANT, TRIAL AND ASSOCIATED METHOD" filed concurrently herewith which are incorporated herein by reference.

TECHNICAL FIELD OF THE INVENTION

The present invention relates generally to the field of orthopaedics, and more particularly, to an implant for use in arthroplasty.

BACKGROUND OF THE INVENTION

The invention relates to implantable articles and methods for implanting such articles. More particularly, the invention relates to a bone prosthesis instrument and a method for using the same.

There are known to exist many designs for and methods for implanting implantable articles, such as bone prostheses. Such bone prostheses include components of artificial joints, such as elbows, hips, knees and shoulders. An important consideration in the design and implanting of virtually any implantable bone prosthesis is that the bone have adequate fixation when implanted within the body.

Earlier designs of implantable articles relied upon the use of cement, such as polymethylmethacrylate (PMMA) to anchor the implant. The use of such implants can have some advantages, such as providing fixation that does not develop free play or does not lead to erosion of joining faces postoperatively. However, the current trend is to use the cements to a lesser extent because of their tendency to lose adhesive properties over time and the possibility that cement contributes to wear debris within a joint.

Recently, implantable bone prostheses have been designed such that they encourage the growth of hard bone tissue around the implant. Such implants are often implanted without cement and the bone grows around surface irregularities, for example, porous structures on the implant.

One such implantable prosthesis is a shoulder prosthesis. During the lifetime of a patient, it may be necessary to replace the natural humeral head and associated glenoid cavity with a prosthesis. Such a shoulder replacement procedure may be necessary to be performed on a patient as a result of, for example, disease or trauma, for example, disease from osteoarthritis or rheumatoid arthritis.

Most shoulder replacement surgeries today involve the implantation of a total shoulder prosthesis. In a total shoulder replacement procedure, a humeral component having a head portion is utilized to replace the natural head portion of the upper arm bone or humerus. The humeral component typically has an elongated intramedullary stem which is utilized to secure the humeral component to the patient's humerus. In such a total shoulder replacement procedure, the natural glenoid surface of the scapula is restructured or otherwise replaced with a glenoid component that provides a bearing surface for the head portion of the humeral component.

With the average age of patients requiring shoulder arthroplasty decreasing, orthopaedic implant manufacturers are developing "bone-sparing" implants for the initial treatment of degenerative arthritis. While bone-sparing implants for the treatment of hip and knee arthroplasty are becoming quite common, bone-sparing shoulder arthroplasty techniques and prostheses are also being developed.

Shoulder surface replacement prostheses are being developed to replace the articulating surface of the proximal humerus with a minimal bone resection and minimal disruption of the metaphysis and the diaphysis. Current designs use a semi-spherical articular dome with a small stem for rotational stability. The under surface of the articular head is also semi-spherical and meets with a spherically machined humeral head.

Typically, however, arthritis of the gleno-humeral joint causes flattening of the humeral head with a large medial osteophyte. The flat humeral head can cause voids in the bone under the prosthesis resulting in limited contact between the prosthesis and the resected bone and may limit the load transfer capability between the prosthesis and the humerus.

Referring now to FIG. 2, a healthy long bone or, in the form of, for example, a humerus 1 is shown. The humerus 1 includes a head 2 on the proximal end of the humerus 1. The head 2 of a healthy humerus has an arcuate outer periphery. The arcuate outer periphery is generally hemispherical and meets with a concave glenoid cavity 3.

Referring now to FIG. 3, a diseased humerus 4 is shown. The diseased humerus 4 includes a head 5. The head 5 is flattened as shown in FIG. 3. The humerus 4 also has developed a large medial osteophyte 7.

Referring now to FIG. 4, a prior art prosthesis 8 is shown in position on the head 5 of diseased humerus 4. The head 5 includes a flattened humeral head area or bony defect 9 that leads to a void 6 between the prosthesis 8 and the bony defect 9.

Great variations in the size of a patient's humerus and the humeral head of that humerus, as well as variations in the progress of the arthritis or other disease that leads to the flattening of the humeral head results in a large variation in the amount of void in the bone under the prosthesis. Determining the amount of void in the humeral head is, therefore, important but yet, difficult to determine. Radiographic techniques including x-rays can be used to determine the shape of a long bone, for example, a humerus. Such x-rays, however, only portray the broad outline of the humerus and may not accurately show the shape of the defect.

There is a need, therefore, for a better method of determining the size of the void under the bone of a prosthesis caused by the flattening of the humeral head from osteoarthritis or other degenerative bone diseases.

SUMMARY OF THE INVENTION

The present invention includes a proposed instrument that may be used to size the humeral head for a surface replacement prosthesis. The instrument may also be used to determine the appropriate amount of resection of the humeral head. The device further can be used to determine the required thickness of augmentation spacers that may be used with the surface replacement prosthesis for replacing the missing bone. The instrument of the present invention may also be used to determine the placement of a guide rod to align cutting tools used for preparing the humeral head for the fitting of a humeral prosthesis.

According to one embodiment of the present invention, a gauge for measuring bone contour of a bone for use in joint arthroplasty is provided. The gauge includes a body and a probe. The body has a body contact portion of the body for contact with the bone. The probe is movably positional with respect to the body. The probe includes a probe contact portion for contact with the bone. The relative position of the probe with respect to the body is indicative of the contour of the bone.

According to another embodiment of the present invention, a kit for use in selecting one of a plurality of joint implants for use in joint arthroplasty on a bone is provided. The kit has a first gauge and a second gauge.

The first gauge includes a first gauge body having a portion of the first gauge body for contact with the bone and a first gauge probe. The first gauge probe is movably positional with respect to the first gauge body. The first gauge probe has a portion for contact with the bone. The relative position of the first gauge probe with respect to the first gauge body is indicative of the contour of the bone. The second gauge includes a second gauge body having a portion of the second gauge body for contact with the bone and a second gauge probe. The second gauge probe is movably positional with respect to the second gauge body. The second gauge probe has a portion for contact with the bone. The relative position of the second gauge probe with respect to the second gauge body is indicative of the contour of the bone.

According to yet another embodiment of the present invention, a kit for use in performing joint arthroplasty on a bone is provided. The kit includes a first implant having a first implant surface for contact with the bone. The kit also includes a second implant having a second implant surface for contact with the bone. The second implant has at least one dimension different from the corresponding dimension of the first implant. The kit further includes a first gauge. The first gauge has a first gauge body having a contact portion of the first gauge body for contact with the bone. The first gauge contact portion is shaped to correspond to the first contact surface of the first implant. The kit also includes a second gauge. The second gauge has a second gauge body having a second gauge contact portion of the second gauge body for contact with the bone. The second gauge contact portion is shaped to correspond to the second implant contact surface of the second implant. The first gauge contact portion has at least one dimension that is different from the corresponding dimension of the second gauge contact portion.

According to a further embodiment of the present invention, a method for providing joint arthroplasty is provided. The method includes the steps of providing a gauge for making a measurement of the contour of a long bone, making a measurement of the contour of a long bone with the gauge, providing a plurality of joint prostheses, selecting one of the plurality of joint prostheses based upon the measurement of the contour, and implanting the selected one prosthesis onto the long bone.

The technical advantages of the present invention include an ability to accurately measure the void in the bone of a flattened humerus under the prosthesis. For example, according to one aspect of the present invention, the gauge of the present invention includes a body, which has a contact face with a shape corresponding to that of the interior periphery of the prosthesis to be implanted as well as a probe extending from that body. By measuring the location of the probe relative to the body, an accurate measurement can be made of the void in the natural humerus. Thus, the present invention provides for an accurate measurement of the void of the flattened humeral head.

Another technical advantage of the present invention is the ability to size the humeral head for a surface replacement prosthesis. For example, according to one aspect of the present invention, the gauge of the present invention includes a body which has an internal shape similar to that of the internal shape of the prosthesis, as well as a window in the body of the gauge such that the gauge can be used to determine the appropriateness of a particular sized surface replacement prosthesis. The gauge can be used to obtain a physical feel of the fit of the prosthesis as well as a visual check of the appropriateness of the prosthesis by viewing a bone through the slots in the gauge. Thus, the present invention provides for a tool to size the humeral head for a surface replacement prosthesis.

The technical advantages of the present invention further includes an apparatus and method for determining the required thickness of augmentation spacers for filling the missing bone. For example, according to one aspect of the present invention, the gauge of the present invention includes a body having an internal shape similar to that of the internal shape of the prosthesis, as well as, a probe extending from the inside of the body to contact the flattened humeral head. The probe can be used to determine the required thickness of the augmentation spacers by measuring the position of the probe when it contacts the flattened humerus. Thus, the present invention provides for a method of determining the required thickness of the augmentation spacers.

The technical advantages of the present invention further includes an ability to use the gauge to determine the placement of a guide rod in the bone. The rod can be used to guide an instrument for fitting a prosthesis. For example, according to one aspect of the present invention, the gauge of the present invention includes a body which has an internal periphery similar to that of the prosthesis to be implanted, plus a central opening which slotably fits with a guide rod. The rod can be removed and a self-drilling rod can be placed in the bone to guide an instrument, for example, a reamer. Thus, the present invention provides for a tool to assist in the placement of the guide rod for other machining operations for fitting a prosthesis.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
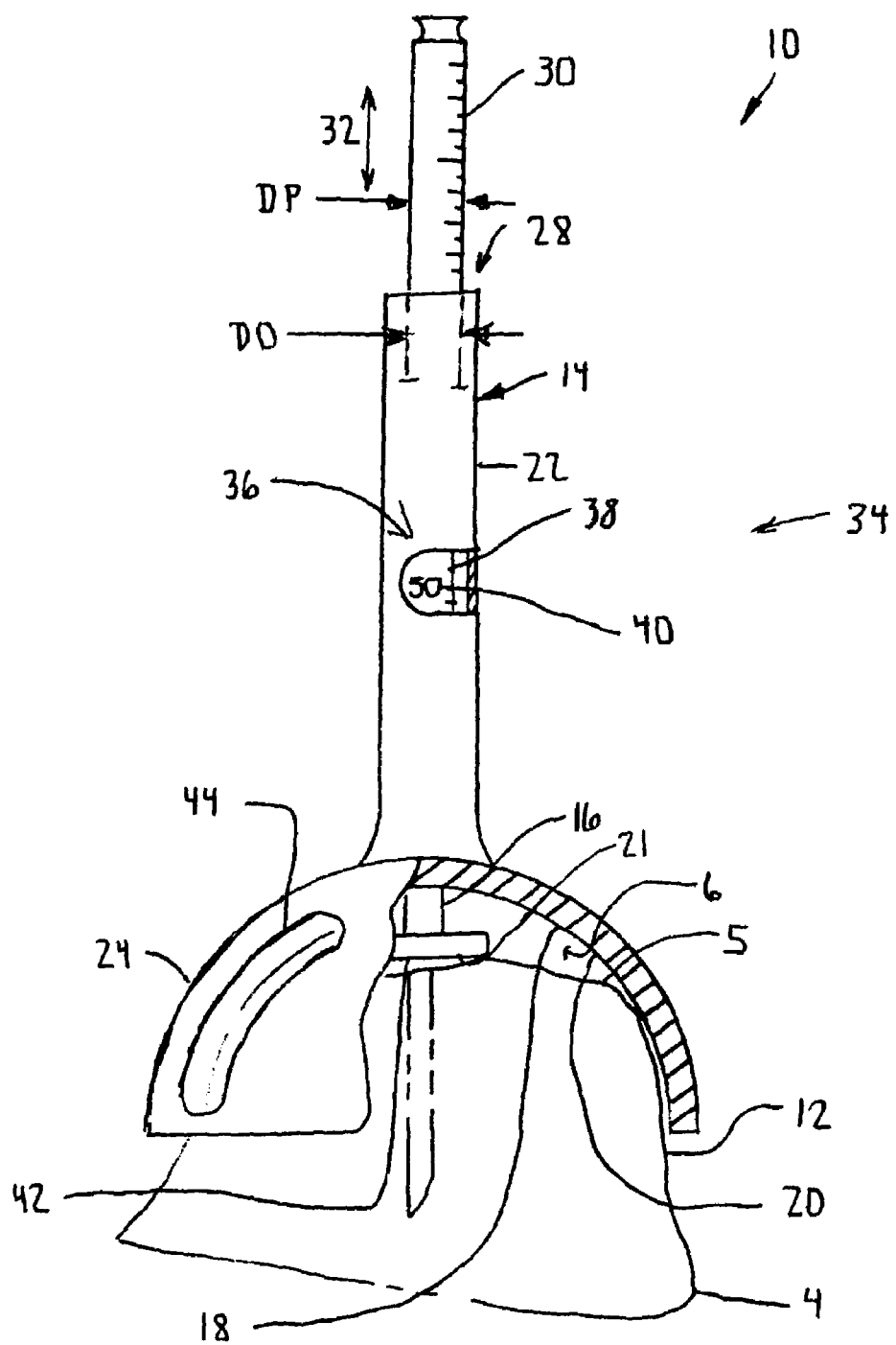
FIG. 1 is a plan view partially in cross section of a gauge according to the present invention for determining the appropriate spacer for a surface replacement prosthesis for use on a diseased humerus.
Figure 2:
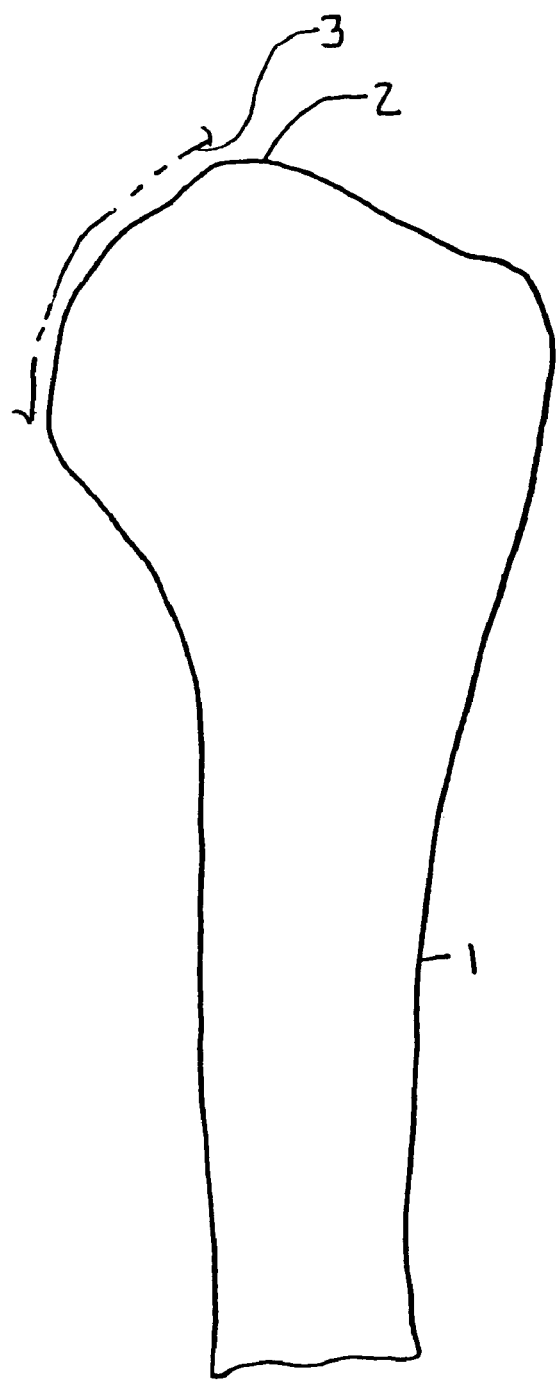
FIG. 2 is a plan view of a healthy humerus.
Figure 3:
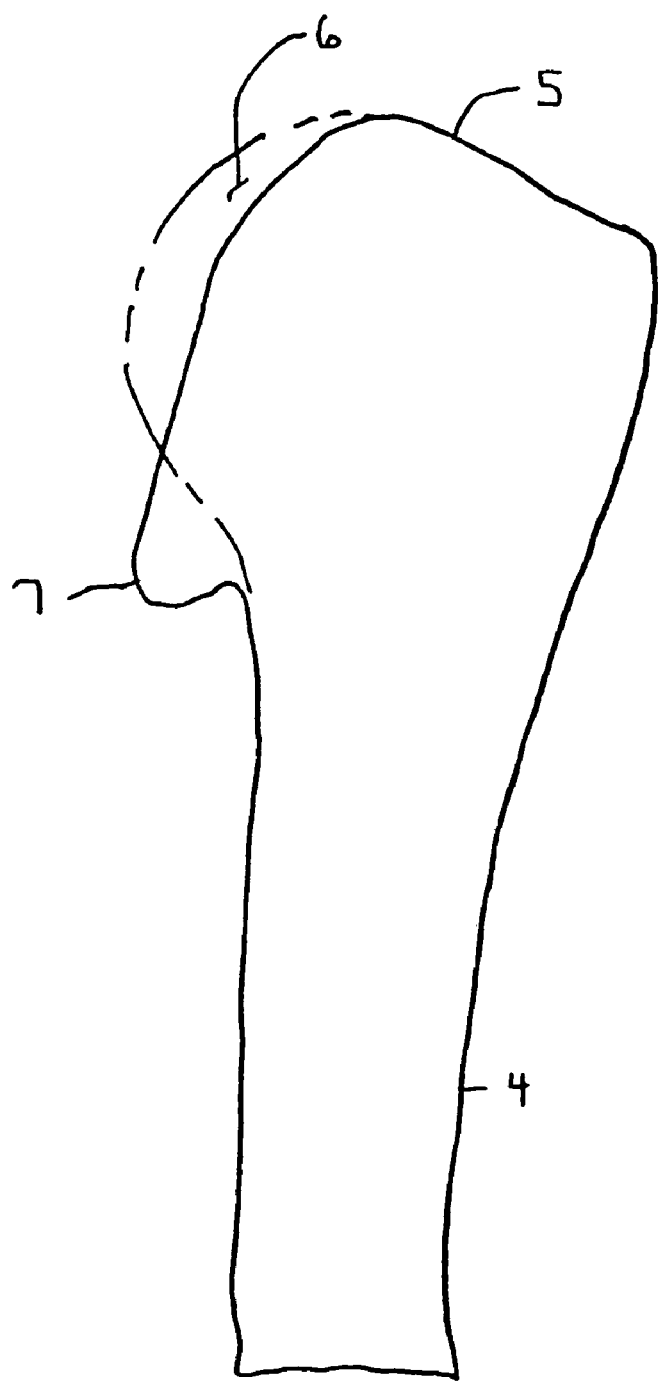
FIG. 3 is a plan view of a diseased humerus.

According to the present invention and referring to FIG. 1, gauge 10 is shown. The gauge 10 is used for measuring bone contour 12 of the bone 4, for example, a humerus, for use in joint arthroplasty. The gauge 10 includes a body 14 and a probe 16. The body 14 has a portion 18 of the body 14 for contact with the bone 4. The probe 16 is movably positional with respect to the body 14. The probe 16 includes a contact portion 21 of the probe 16 for contact with the bone 4. The relative position of the probe 16 with respect to the body 14 is indicative of the bone contour 12 of the bone 4.

The gauge 10 may, as shown in FIG. 1, be such that at least a portion of the portion 18 for contact with the bone 4 includes a contoured portion with a periphery 20 similar to the internal periphery of the prosthesis to be implanted.

The gauge 10 of FIG. 1 may, for example, provide that at least a portion of the body 14 includes a concave surface. As shown in FIG. 1, the internal periphery 20 may be concave. In fact, as shown in FIG. 1, the internal periphery 20 may be hemispherical.

Figure 9:
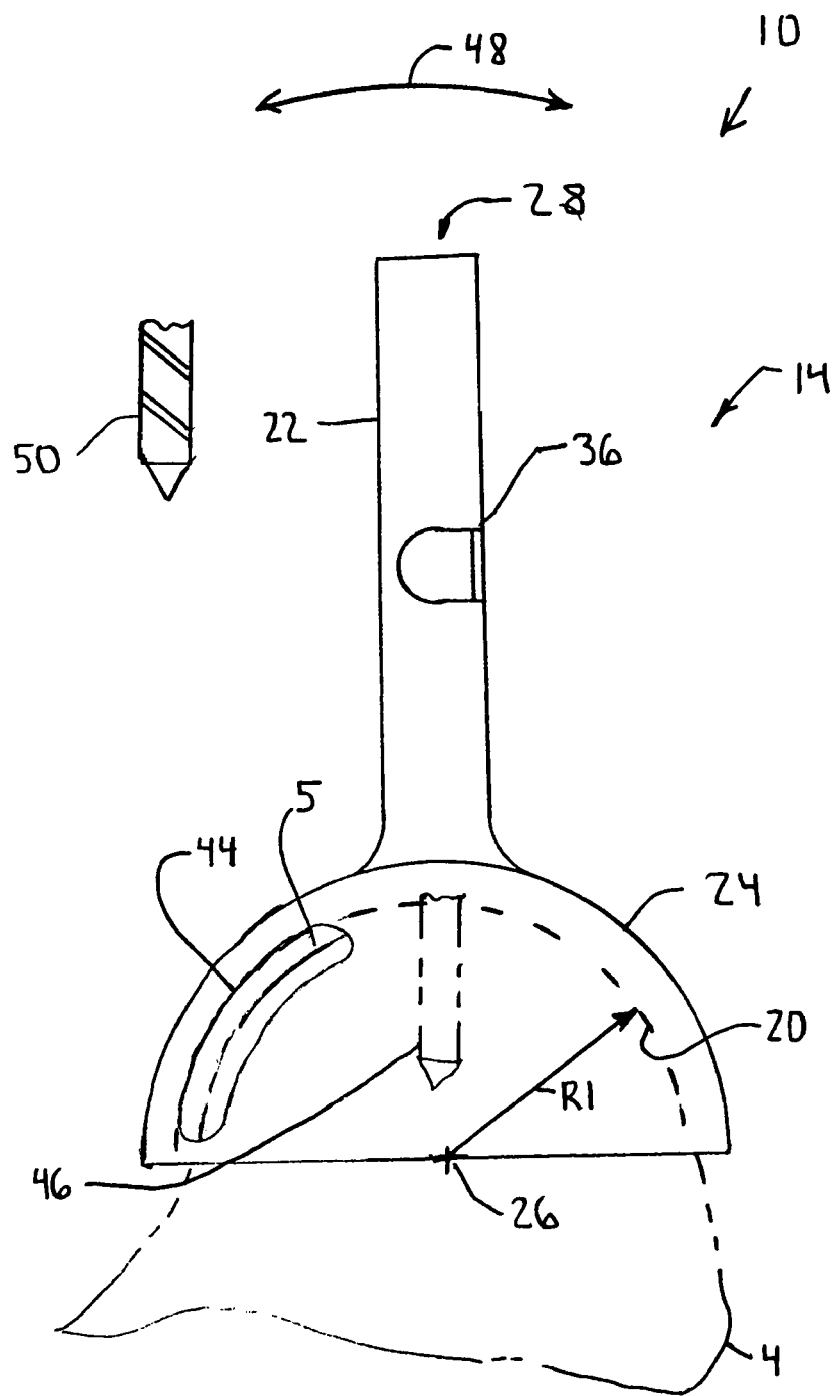
FIG. 9 is a plan view of the housing of the gauge of FIG. 1.

Referring now to FIG. 9, the body 14 of the gauge 10 is shown in greater detail. The body 14 includes a generally hollow cylindrical portion 22 as well as a hollow hemispherical portion 24. As shown in FIG. 9, a radius R1 extending from origin 26 may define the inner periphery 20 of the hemispherical portion 24.

Referring again to FIG. 1, while the probe 16 may be movably positioned with respect to the body 14 in any suitable fashion, as shown in FIG. 1, the body 14 defines a longitudinal opening 28 therein. As shown in FIG. 1, the probe 16 may be slidably fitted into the opening 28.

As shown in FIG. 1, the probe 16 may include a generally cylindrical portion 30 having a diameter, for example, DP. The longitudinal opening 28 may be generally cylindrical defined by a diameter DO. The diameter DP is preferably slightly smaller than the diameter DO to permit the sliding motion of the probe 16 in the direction of arrows 32.

The gauge of the present invention may, as shown in FIG. 1, include indicia 34 located on the body 14 or the probe 16. It should be appreciated that the indicia 34 may be located on both the probe 16 and the body 14. The indicia 34 correspond to the relative position of the probe 16 with respect to the body 14.

As shown in FIG. 1, the body 14 of the gauge 10 may include a body indicia opening 36 for assisting in viewing the indicia 34. The indicia 34 may have any suitable form and may, for example, include marks 38 or characters 40 in the form of, for example, numerals or letters. The marks 38 and the characters 40 may be located on either the body 14 or the probe 16.

As shown in FIG. 1, the gauge 10 includes characters 40 located on the probe 16, and a plurality of marks 38 equally spaced longitudinally along the probe 16, as well as a solitary mark 38 located on the body 14. The alignment of the solitary mark on the body with the corresponding mark 38 on the probe corresponds to the relative position of bone contact surface 42 of the probe contact portion 21 of the probe 16. As shown in FIG. 1, the probe 16 adjacent the bone contact surface 42 may be substantially wider than cylindrical position 30 of the probe 16 in order to obtain a more representative indication of the bone contour 12.

As shown in FIG. 1, the body 14 of the gauge 10 may include a viewing opening 44 for visually sighting the condition of the bone contour 12, while positioning the gauge 10 with respect to the bone contour 12. The viewing opening 44 may have any shape but may, as shown in FIG. 1, be generally elongate and arcuate corresponding to the bone contour 12.

Figure 6:
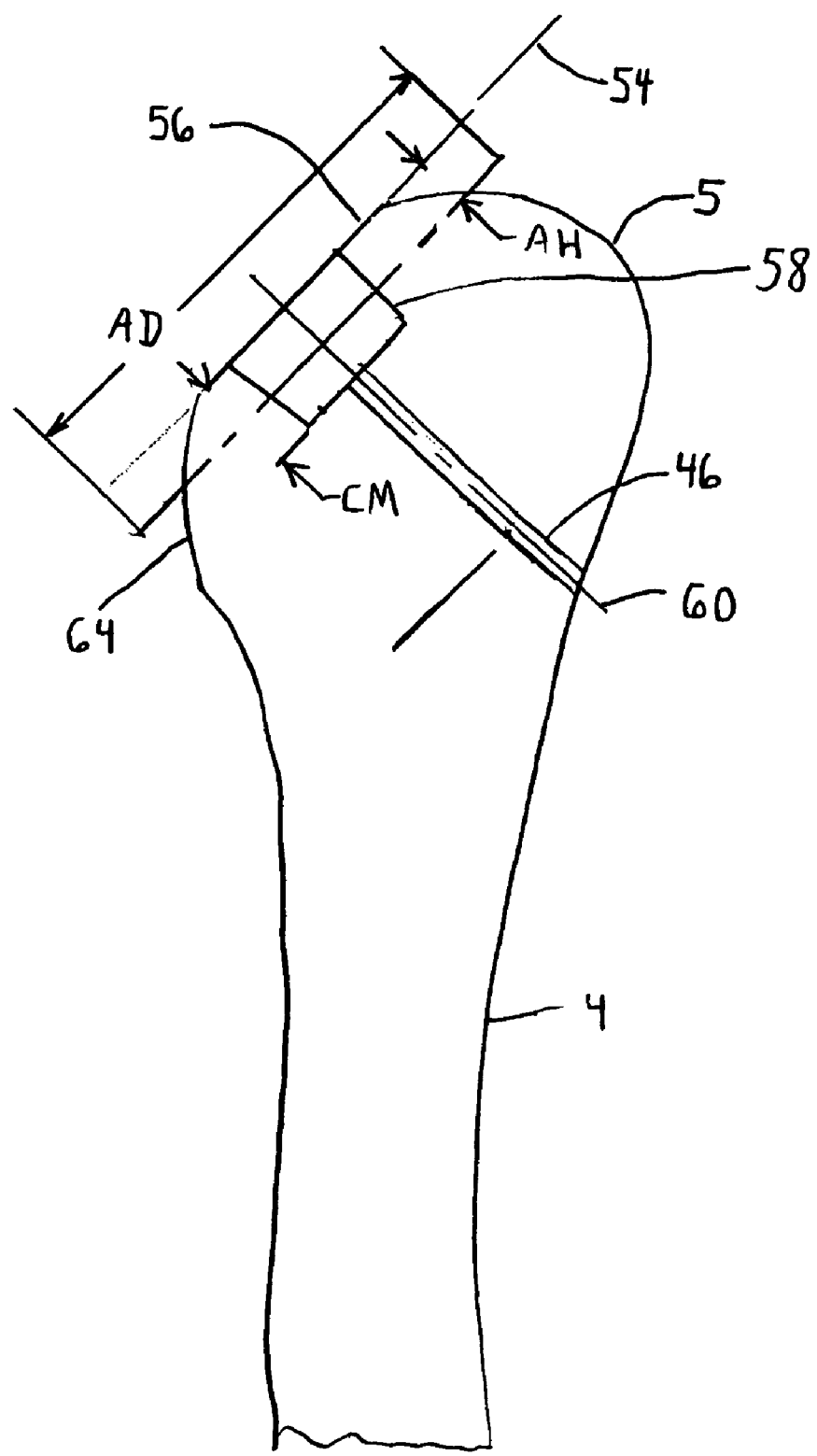
FIG. 6 is a plan view partially in cross section of a resected humerus with a cavity prepared for a prosthesis gauge.

Referring again to FIG. 9, the gauge 10 may provide an additional function to that already mentioned by being able to be used to assist in preparing a locating hole 46 in the head 5 of the humerus 4 (see FIG. 6). The locating hole 46 may be used to guide tools used to prepare the head 5 of the humerus 4 for an appropriate prosthesis. When utilizing the gauge 10 to prepare the locating hole 46, the body 14 of the gauge 10 is brought in a position relative to the head 5 of the humerus 4 by sight as it is located along the bone contour 12 in the direction of arrows 48. Using the viewing window 44, as well as, the cylindrical portion 22 of the body 14 as guides to determine the proper orientation of the locating hole 46. A drill 50 in the form of, for example, a standard spiral point drill having a size compatible for a sliding fit with opening 28 may be inserted through opening 28 and used to form the locating hole 46 after the probe 16 has been removed from the body 14 of the gauge 10.

Figure 10:
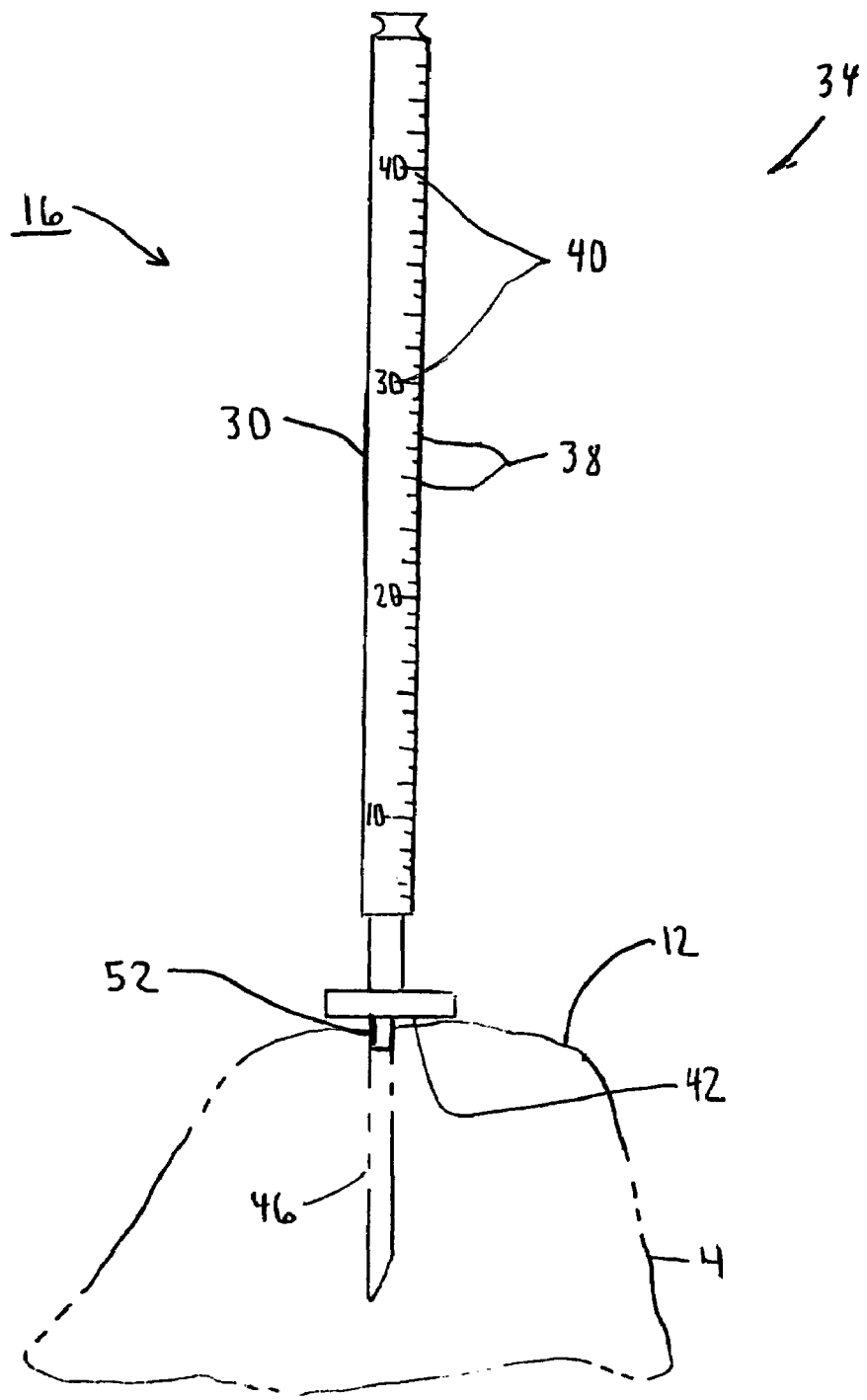
FIG. 10 is a plan view of the probe for use in the gauge of FIG. 1.

Referring now to FIG. 10, the probe 16 is shown in greater detail. As shown in FIG. 10, the indicia 34 include marks 38 that are equally spaced longitudinally along the cylindrical portion 30 of the probe 16. Characters 40 in the form of, for example, numbers are spaced adjacent to some of the marks 38. The characters 40 may be used to indicate a relative position of the bone contact surface 42 of the probe 16 with respect to the body 14 or may be used to represent a particular size of a prosthesis which would be appropriate for that particular bone contour, or to select a particular cutting tool that should be used, or to determine a setting on a cutting tool that should be used to correspond to that particular reading.

To assure that the gauge 10 is properly positioned with respect to the bone contour 12, the probe 16 may include a pilot 52 which may be fitted into the locating hole 46.

Figure 8:
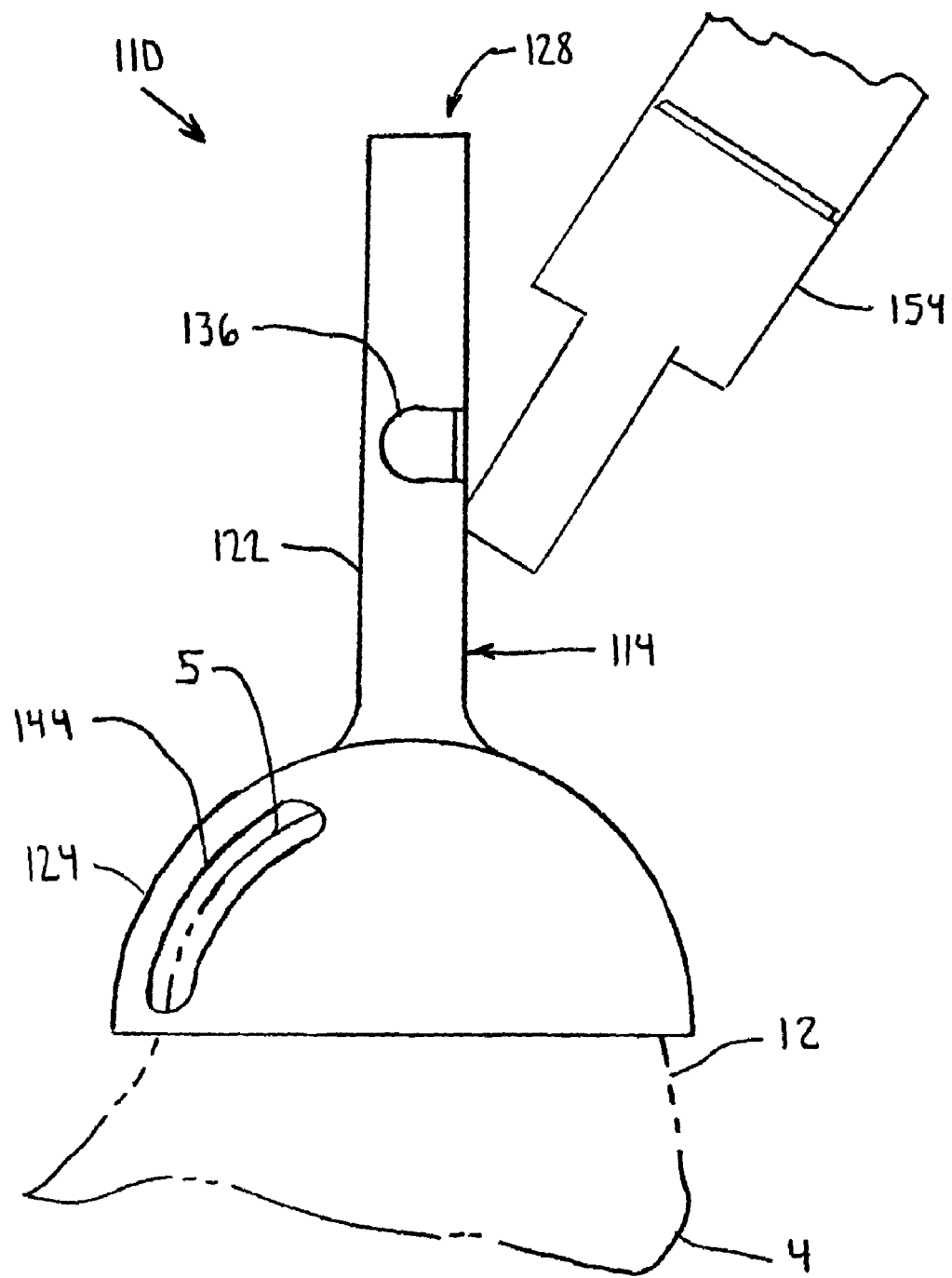
FIG. 8 is a plan view partially in cross section of another embodiment including an offset handle of a gauge according to the present invention for determining the appropriate spacer for a surface replacement prosthesis for use on a diseased humerus.

Referring now to FIG. 8, an alternate embodiment of the present invention is shown as gauge 110. The gauge 110 is similar to the gauge 10 of FIG. 1, except that the gauge 110 is designed to assist in the ease of viewing the position of the gauge with respect to the bone contour 12. When utilizing the gauge 10 of FIG. 1, the cylindrical portion 22 of the body 14 serves as the handle for the gauge 10. When gripping the gauge 10 by the handle 22, the viewing window 44 is obstructed by the person's hand. Thus, when utilizing the gauge 10 the viewing of the window 44 to assist in determining the proper position of the head 5 with respect to the gauge may be more difficult. Therefore, gauge 110 is designed to alleviate the viewing window problem.

As shown in FIG. 8, the gauge 110 includes a body 114 having a cylindrical portion 122 similar to the cylindrical portion 22 of the gauge 10 of FIG. 1. The body 114 further includes a hollow hemispherical portion 124 similar to the portion 24 of the gauge 10. The cylindrical portion 122 includes a longitudinal cylindrical opening 128 as well as an indicia opening 136. The hemispherical portion 124 includes a viewing window 144 to view the head 5 in assisting the proper positioning of the gauge 110.

As shown in FIG. 8, the gauge 110 includes a separate handle 154 separate from the cylindrical body 122. The handle 154 is utilized for holding the gauge 110 in position with respect to the head 5. It can be seen that the handle 154 is preferably opposed to the viewing window 144 so that the head 5 may be clearly viewed through the viewing window 144 while the gauge 110 is being held by the handle 154.

Figure 5:
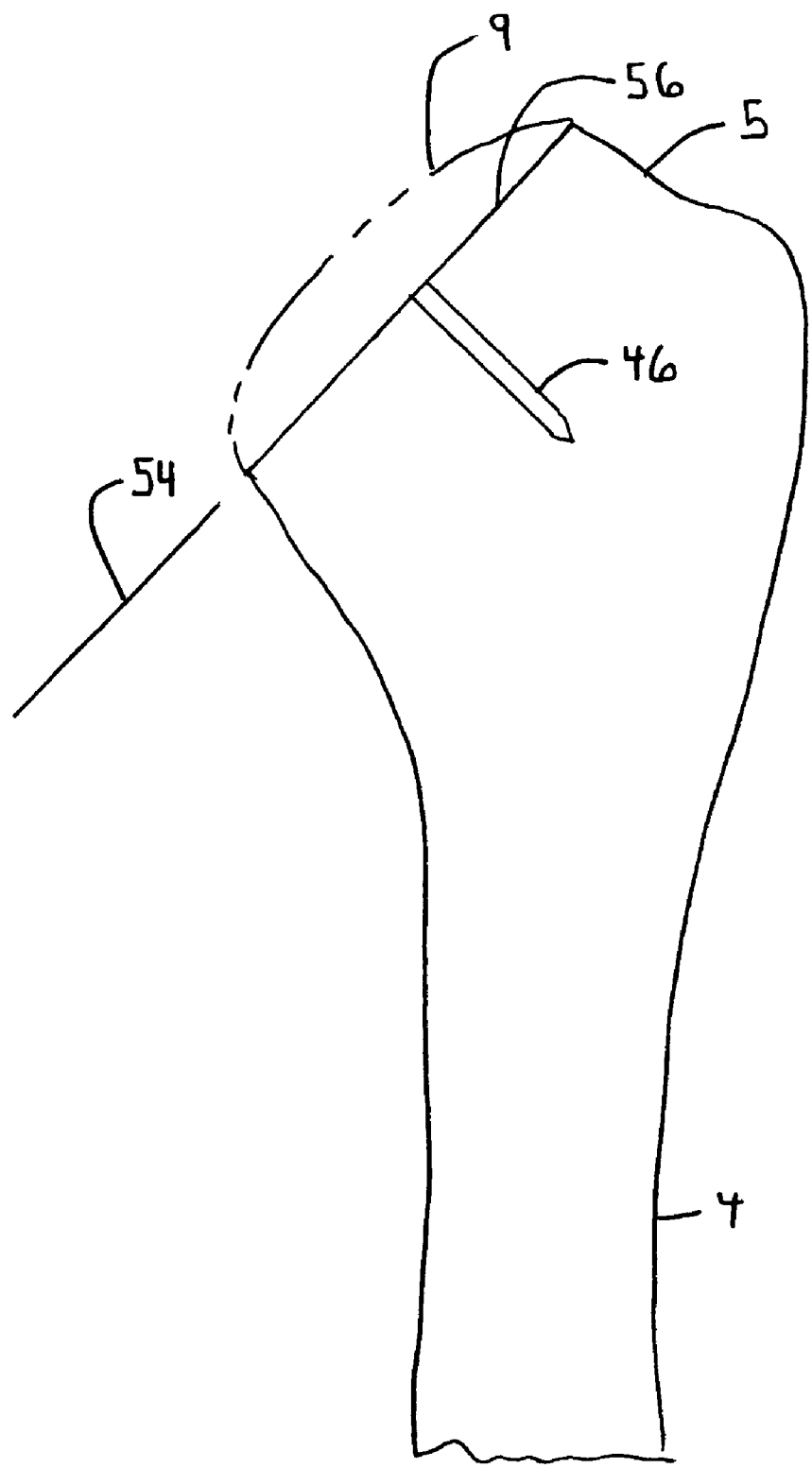
FIG. 5 is a plan view of a resected humerus showing the resected portion in phantom.
Figure 7:
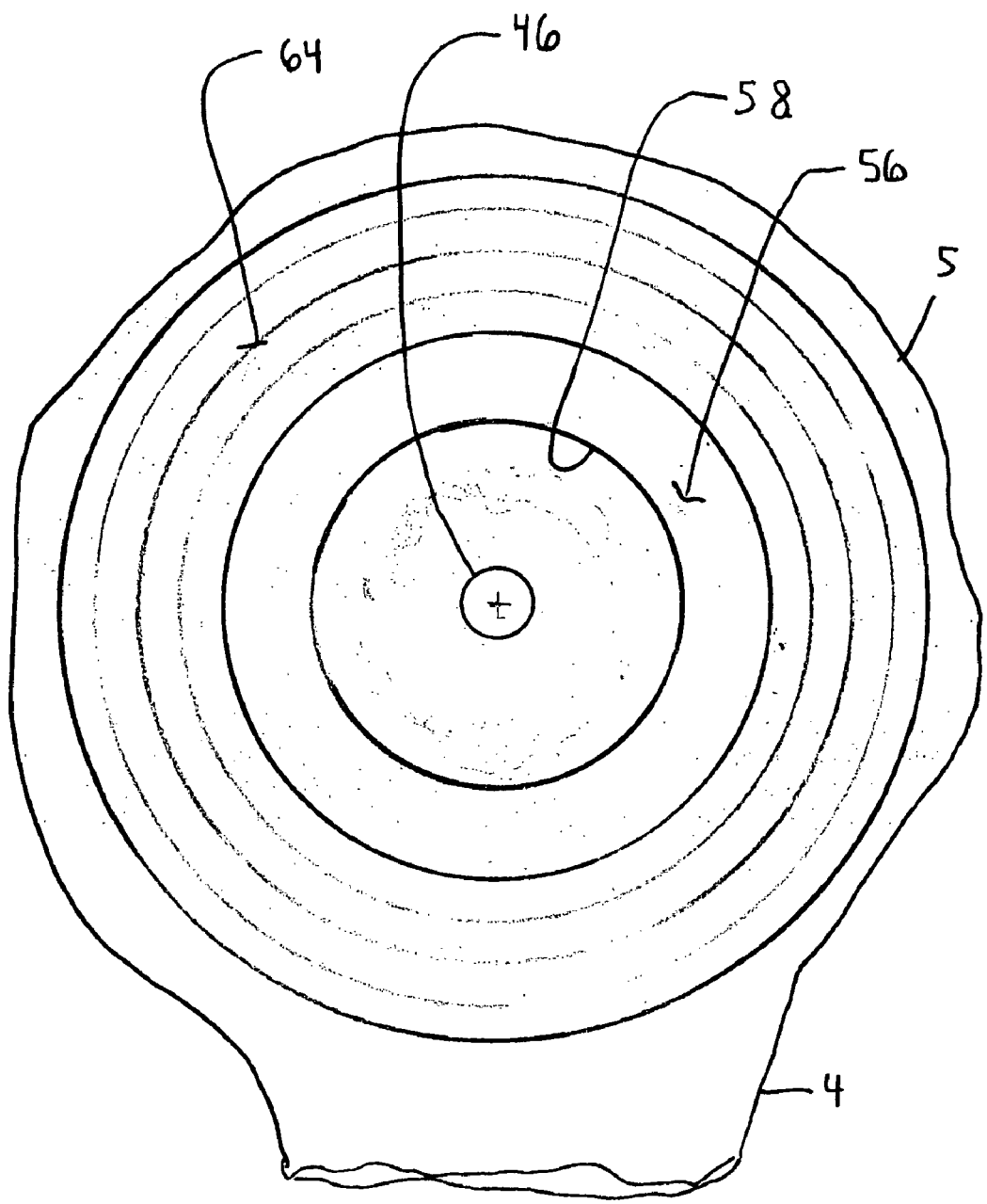
FIG. 7 is an auxiliary view of resected humerus with a cavity of FIG. 6.

Referring now to FIGS. 5, 6 and 7, a long bone in the form of a humerus 4 is shown in varying stages of preparation for receiving a prosthesis utilizing the gauge of the present invention, as well as the surgical method of the present invention.

Figure 4:
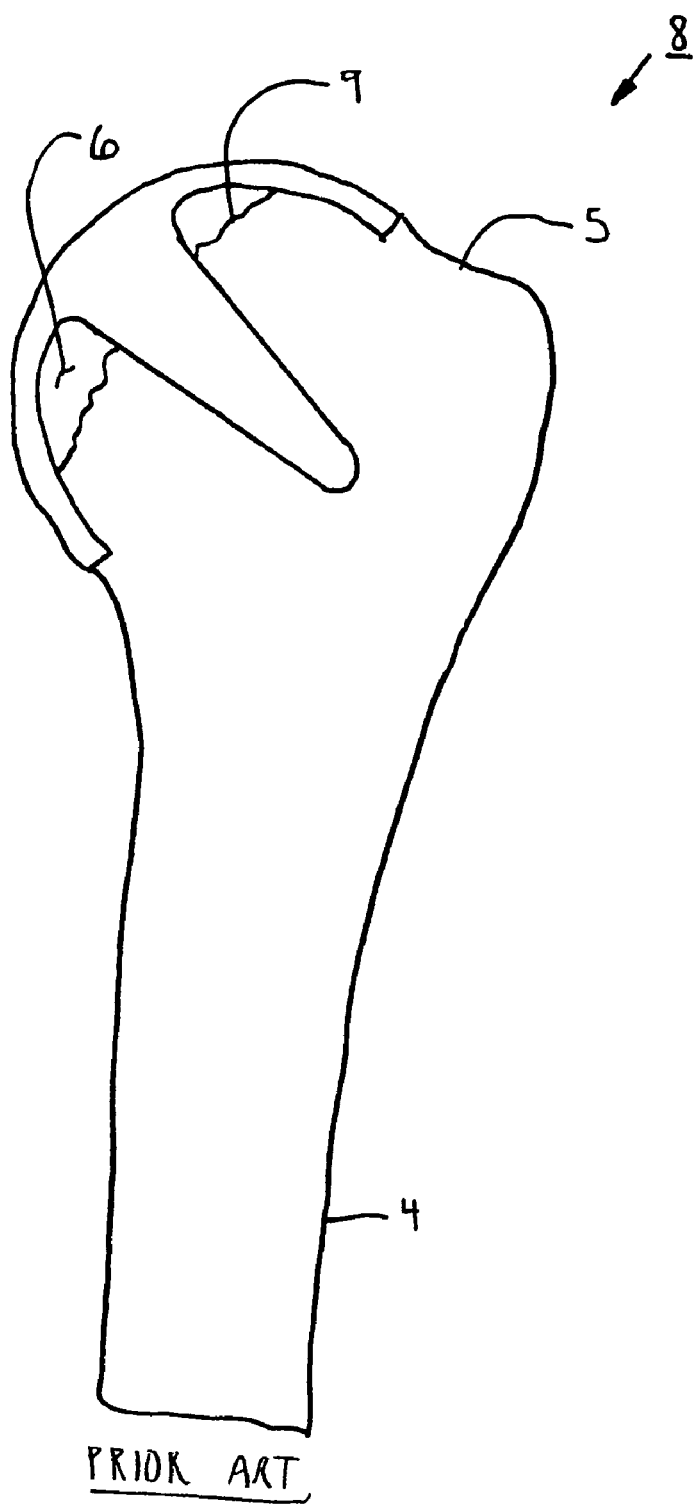
FIG. 4 is a plan view partially in cross section of a prior art humeral prosthesis.

Referring to FIG. 5, the humerus 4 is shown with a portion of the flattened head 5 resected. The head 5 is resected along resection line 54 providing a resected surface 56. The surface 56 may be resected by any suitable method, for example, a reamer, a mill end cutter, a saw, or an osteotome. The location of the resection line 54 may be determined by utilizing the gauge 10 of FIG. 4. The indicia 34 on the gauge 10 of FIG. 1 may be utilized to determine the position of the resection line 54 and the proper depth of the surface 56.

Referring now to FIGS. 6 and 7, the long bone in the form of humerus 4 is shown with the head 5 being prepared for a prosthesis used in conjunction with the gauge and surgical procedure of the present invention. The prosthesis for use with the gauge and surgical method of the present invention may include a stem (not shown) for securing the prosthesis to the humerus 4.

To accommodate the stem, a tapered securing or mounting hole 58 may be prepared in the humerus 4. The mounting hole 58 may have a generally tapered cylindrical shape having a longitudinal centerline 60 perpendicular to the surface 56.

Any suitable tool may be utilized to form the mounting hole 58. For example, the mounting hole 58 may be machined into the humerus 4 by the use of a reamer. The mounting hole 58 may be positioned a depth CM from the resection line 54. The dimension CM may be established utilizing the gauge 10 of FIG. 1. The gauge 10 of FIG. 1 may establish the proper prosthesis for a given bone contour and the dimension CM may correspond to that recommended for that particular prosthesis.

The preparation of the head 5 of the humerus 4 may further include an arcuate support surface 64 formed adjacent the head 5. The arcuate surface 64 preferably conforms to that of the prosthesis and is generally arcuate and may be generally hemispherical. The arcuate surface 64 may be applied into the humerus 4 in any suitable fashion. For example, the arcuate surface 64 may be machined by a grater-type reamer.

The position of the arcuate surface 64 may be determined by, for example, a depth AH at a diameter AD. The dimensions AD and AH may be determined with the assistance of the gauge 10 of FIG. 1. For example, the gauge 10 may be utilized to determine the proper prosthesis and the dimensions AH and AD may be determined upon that particular prosthesis.

It can be seen that the gauge 10 of FIG. 1, as well as the gauge 110 of FIG. 8 may be used to select the proper amount of resection to the humeral head and, correspondingly, the proper prosthesis to be used for that particular resection. It should be appreciated that due to the variations in the size of the patient and his or her respective humerus, a wide variety of prostheses may be required to accommodate the variations in a patient's humerus.

The gauge 10 of FIG. 1 and the gauge 110 of FIG. 8 may be made of any suitable, durable material that may be sterilized by current sterilization techniques. For example, the gauge can be made of metal, for example, a stainless steel alloy, a cobalt chromium alloy or a titanium alloy.

Not only may the selection of a proper prosthesis be governed by the proper radius of the articulating surface, variations in the progress of the osteoarthritis may result in the flattening of the head of the humerus being in various stages of progression. Due to the changes in the progression of the disease and the resulting shape of the humeral head, the resection plane may vary from being somewhat shallow to being much deeper into the humerus. Therefore, even for a given size of the articulating surface of the prepared natural humerus, the position of the resection, including the planar part of the resection of the humerus, may vary. The need to provide for patient variations may be accomplished by providing a wide variety of sizes and configurations of the prosthesis. The availability of a wide variety of sizes and configurations of prostheses may be quite costly both in small manufacturing lot sizes, as well as in excess inventory. The applicants have discovered that the prosthesis may be made with more than one component.

Figure 11:
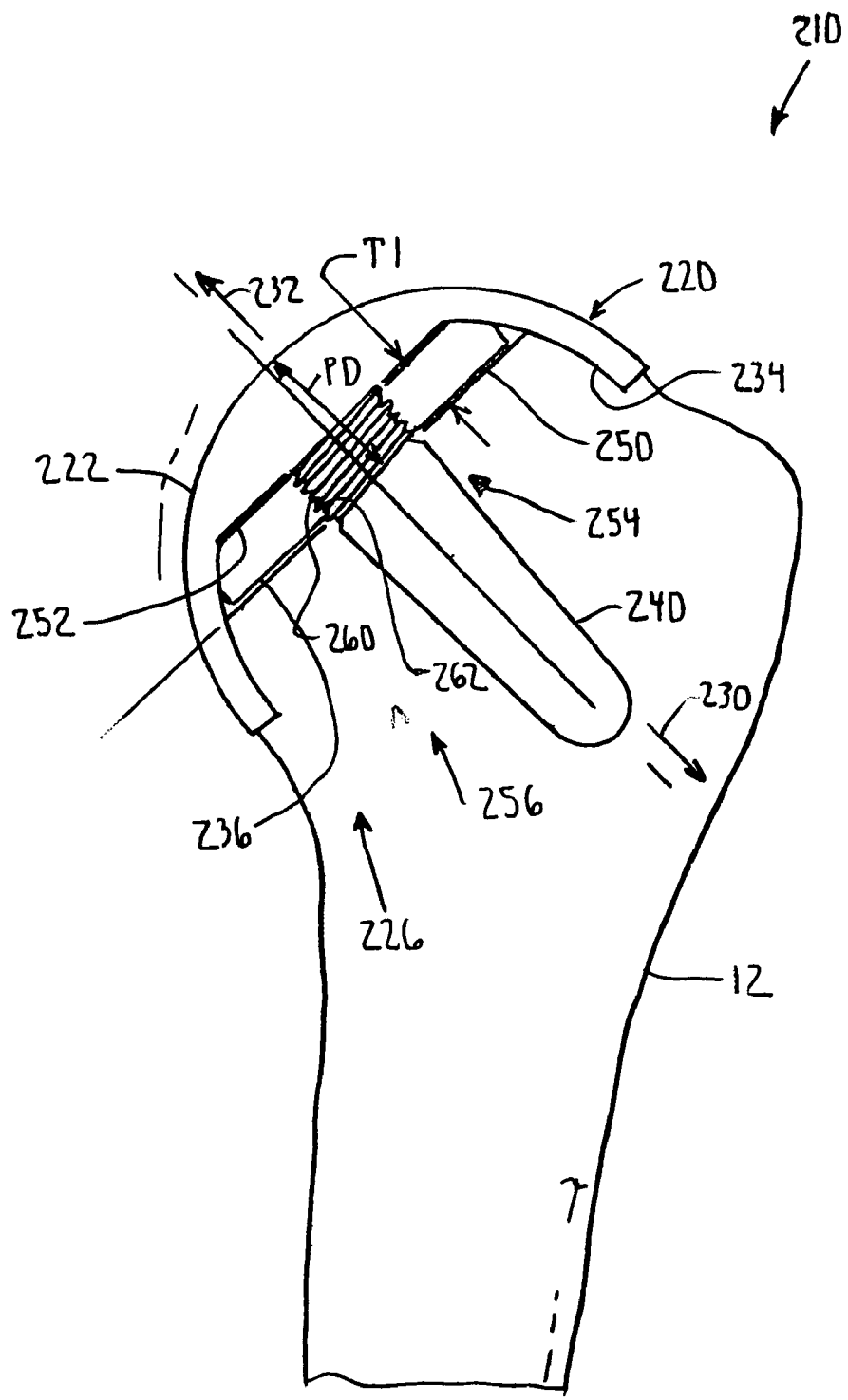
FIG. 11 is a plan view partially in cross section of a surface replacement prosthesis with a screwed-on spacer for which the gauge of the present invention may be utilized to determine the appropriate size of the spacer.

For example, and referring now to FIG. 11, a prosthesis 210 is shown which includes a plurality of components. As shown in FIG. 11, the prosthesis 210 includes in addition to a body 220, a spacer 250. The spacer 250 provides for a variety of locations of the planar portion 56 of the support surface of the long bone or humerus 4 (see FIG. 7). Thus, by utilizing the prosthesis 210, a common body 220 may be used with a variety of spacers 250 having different thicknesses T1. Thus, for any prosthesis 210 a plurality of planar dimensions PD may be provided by merely changing the spacer 250 to either a thinner or a thicker spacer.

For simplicity, the gauge 10 of FIG. 1 and the gauge 110 FIG. 8, may be designed such that the indicia 34, for example the numerals 40, may directly correspond to a particular thickness, part number or other reference to a particular spacer with the appropriate thickness. Thus, the gauge 10 of FIG. 1 may be used to directly determine the particular spacer to be used for a particular humerus 4.

As shown in FIG. 11, the prosthesis 210 includes the body 220. The body 220 includes an articulating surface 222 extending in a second direction 232 as well as a stem 240 extending in a first direction 230 opposed to the second direction 232.

As shown in FIG. 11, the body 220 includes a body planar surface 252 to which the spacer 250 is placed. The spacer 250 defines planar portion 236 of support surface 226 and works in conjunction with arcuate surface 234 of the body 220 to support the prosthesis 210 against the humerus wall.

As shown in FIG. 11, the spacer 250 preferably has a pair of spaced apart parallel faces defined with thickness T1. The spacer 250 has a central opening 254 to permit the spacer 250 to be positioned in place against the body planar surface 252 with the stem 240 passing through the opening 254.

Preferably, and as shown in FIG. 11, the spacer 250 is secured to the body 220 by, for example, a connector 256. The connector 256, may, as shown in FIG. 11, be in the form a threadable connection. For example, the connector 256 may include external threads 260 located on the distal portion of the stem 240. The external threads 260 on the stem 240 cooperate with matching internal threads 262 on the spacer 250. A feature, not shown, in the form of, for example, a recess on the planar portion 236 of the spacer 250 may be utilized to secure the spacer 250 against the body 220. The body 220 and the spacer 250 may be made of any suitable durable material that is compatible with the human body. For example, the body 220 and the spacer 250 may be made of a durable plastic, a ceramic or a metal. If made of a metal, the body 220 and the spacer 250 may be made of, for example, a cobalt chromium alloy, a titanium alloy, or a stainless alloy.

Figure 12:
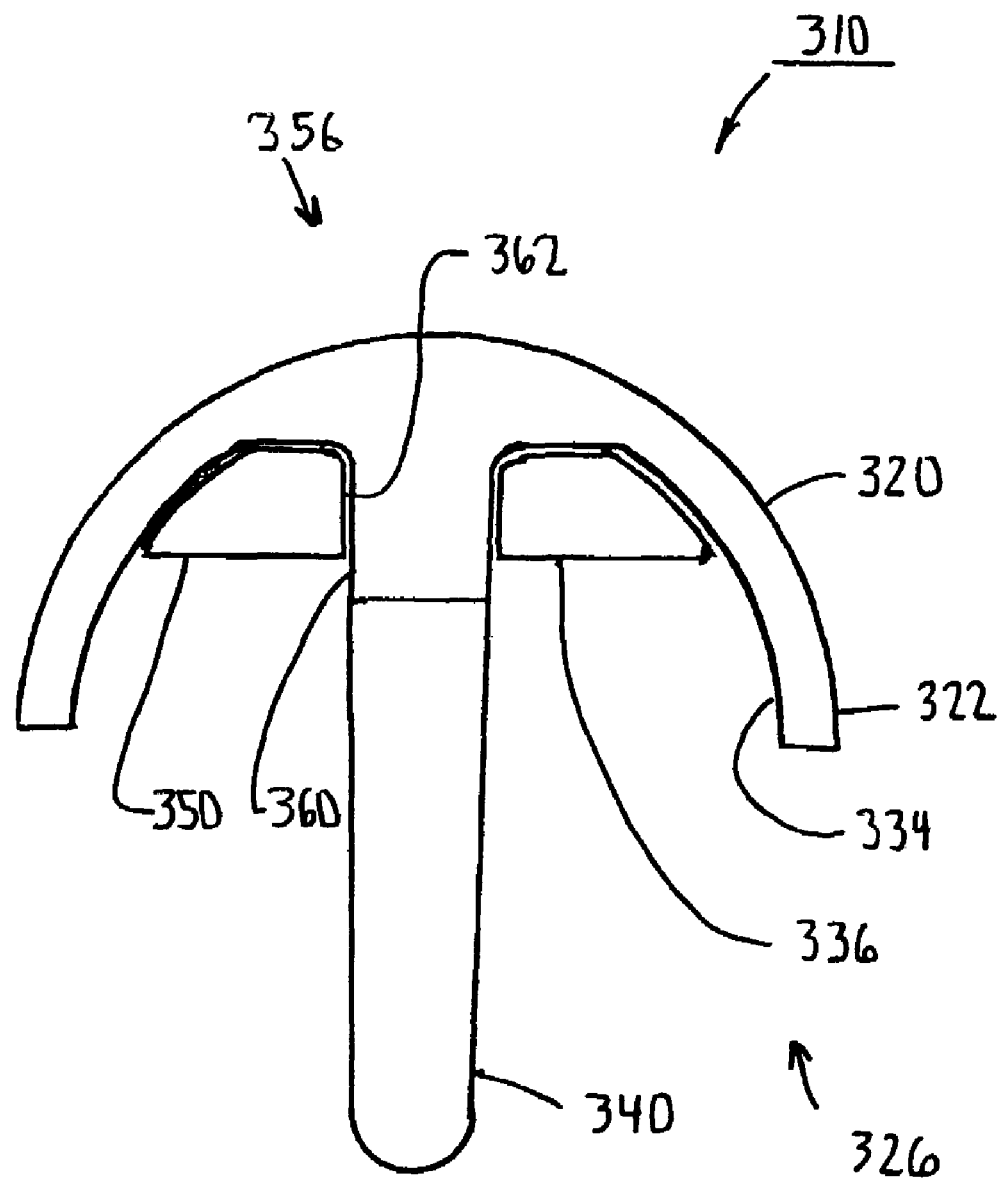
FIG. 12 is a plan view partially in cross section of another embodiment of a surface replacement prosthesis with a tapered fit spacer for which the gauge of the present invention may be utilized to determine the appropriate size of the spacer.

Referring now to FIG. 12, an alternate prosthesis for use with the gauge of the present invention is shown as prosthesis 310. Prosthesis 310 includes a body 320 similar to the body 220 of the prosthesis 210 of FIG. 11 in that the body 320 includes stem 340 similar to stem 240 of FIG. 11. The prosthesis 310 further includes a spacer 350 similar to the spacer 250 of the prosthesis 210 of FIG. 11.

The spacer 350 is secured to the body 320 by means of a connector 356. The connector 356 is different than the connector 256 of the prosthesis 210 in that the connector 356 is in the form of a taper fit. The spacer 350 includes a tapered opening 362 that engages with tapered stem portion 360 of the stem 340 of the prosthesis 310. The body 320 includes an articulating surface 322 and an opposed arcuate support surface 334. The spacer 350 includes a planar support surface 336 which, together with the arcuate support surface .334, form the support surface 326 for supporting the prosthesis 310 within the humerus.

Figure 13:
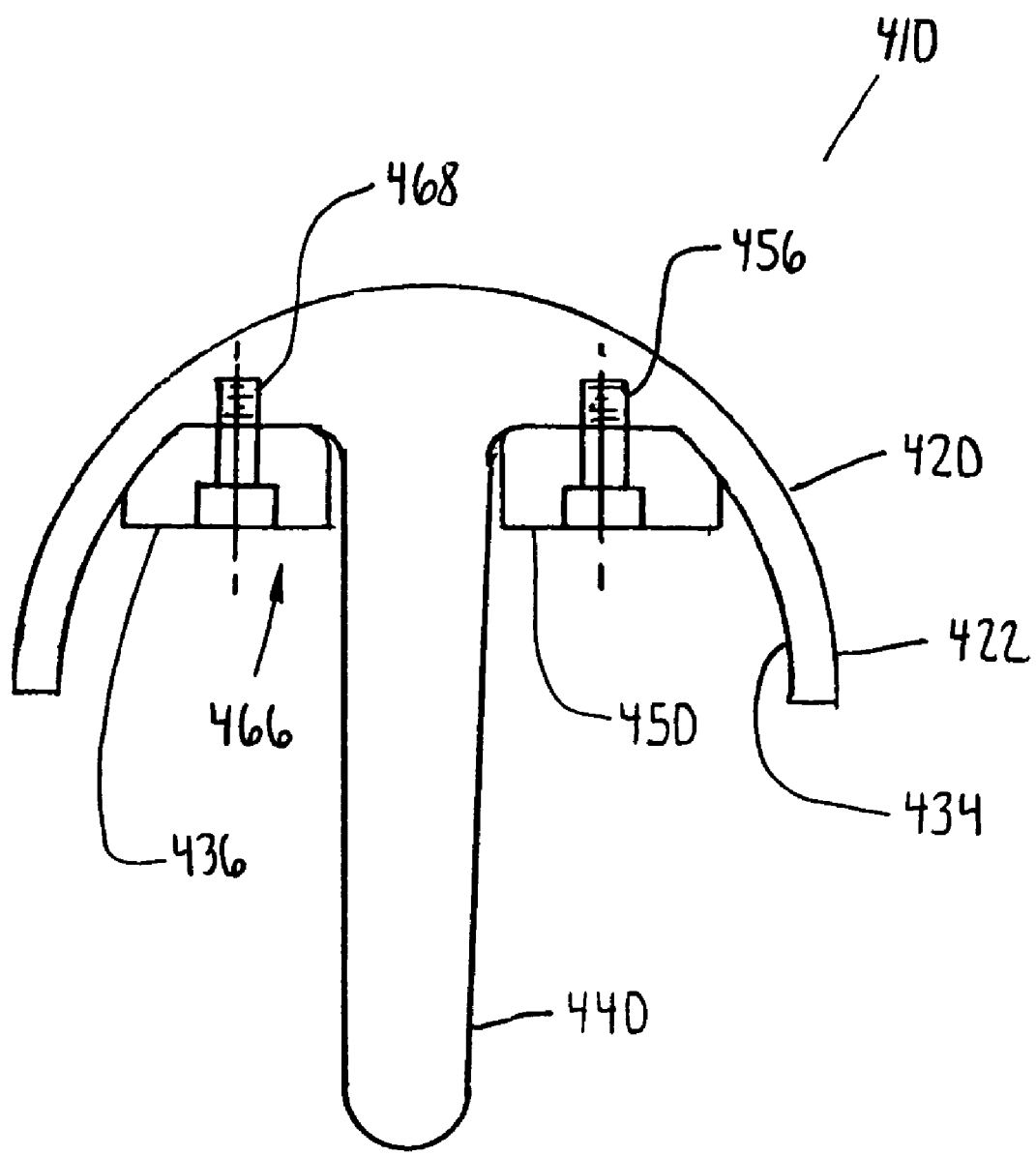
FIG. 13 is a plan view partially in cross section of another embodiment of a surface replacement prosthesis with a bolted-on spacer for which the gauge of the present invention may be utilized to determine the appropriate size of the spacer.

Referring now to FIG. 13, an alternate prosthesis for use with the gauge of the present invention is shown as prosthesis 410. The prosthesis 410 of FIG. 13 is similar to the prosthesis 310 of FIG. 12, and includes a body 420 similar to the body 320 of FIG. 12. The body 420 includes an articulating surface 422 and an opposed arcuate support surface 434. The body 420 in integral with a stem 440 similar to the stem 340 of FIG. 12. The prosthesis 410 further includes a spacer 450 similar to the spacer 350 of the prosthesis 310 of FIG. 12.

The spacer 450 is secured to the body 420 of the prosthesis 410 by means of a connector 456 that is different than the connector 356 of the prosthesis 310 of FIG. 12. The connector 456 is in the form of a plurality of socket head hex cap screws. The cap screws 456 are fitted into recessed openings 466 in the spacer 450. The cap screws 456 are secured to the body 420 by a plurality of threaded openings 468. The spacer 450 provides planar support surface 436.

Figure 14:
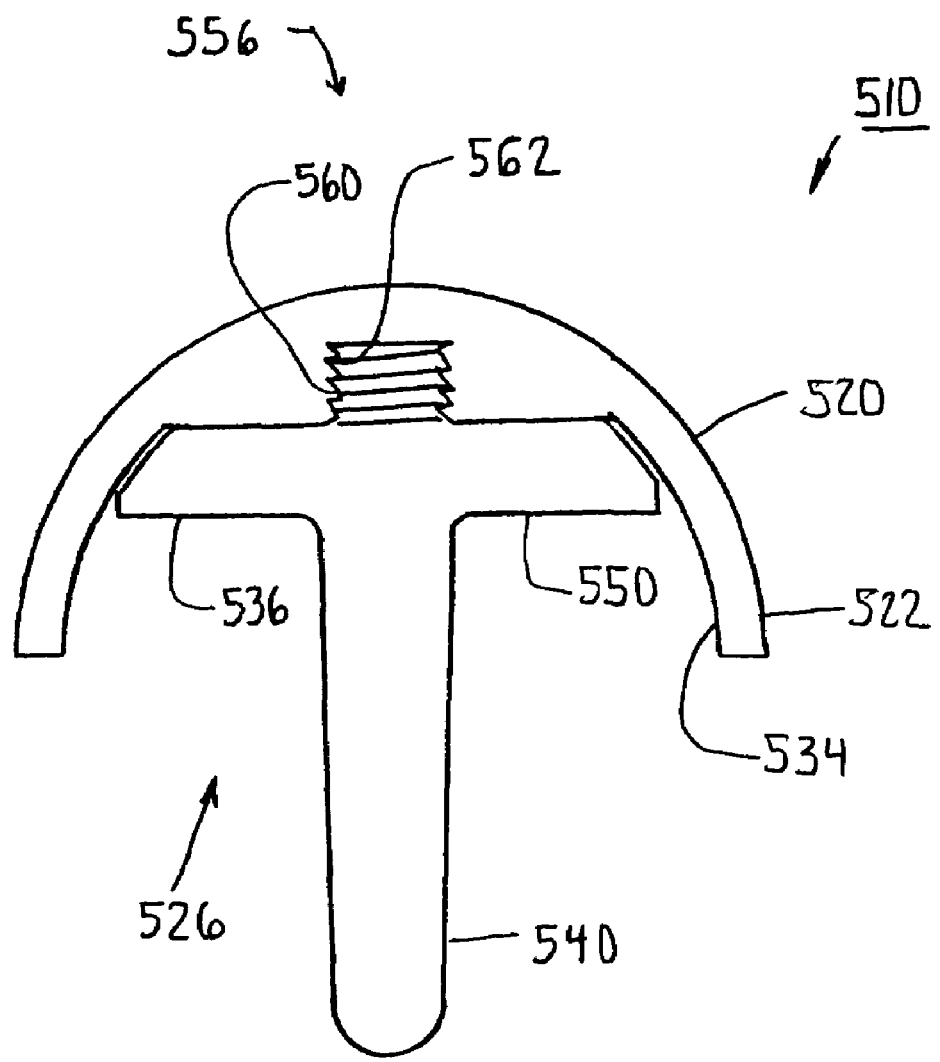
FIG. 14 is a plan view partially in cross section of another embodiment of a surface replacement prosthesis with a bolted-on spacer and stem for which the gauge of the present invention may be utilized to determine the appropriate size of the spacer.

Referring now to FIG. 14, an alternate prosthesis for use with the gauge of the present invention is shown as prosthesis 510. Prosthesis 510 is similar to the prosthesis 210, 310 and 410 in that the prosthesis 510 includes a body 520, a spacer 550, and a stem 540. The prosthesis 510 is different than the prosthesis 210, 310 and 410 in that the spacer 550 and the stem 540 are integral with each other. The body 520 of the prosthesis 510 thus does not include the stem 540 and is a separate part from the spacer 550 and the stem 540.

As shown in FIG. 14, the body 520 has a generally hollow hemispherical shape having a articulating surface 522 and an opposed arcuate support surface 534. The spacer 550 has a general disc shape with the stem 540 having a generally cylindrical shape and extending outwardly from the center portion of the spacer 550. The spacer 550 is secured to the body 520 by means of a connector 556.

The connector 556 as shown in FIG. 14 is in the form of a threaded stem extending from the spacer 550 in a direction opposed to the stem 540. The connector 556 includes external threads 560 that mate with internal threads 562 in the body 520. The spacer 550 forms planar support surface 536 that together with the arcuate support surface 534 forms support surface 526 for supporting the prosthesis 510 against the humerus.

Figure 15:
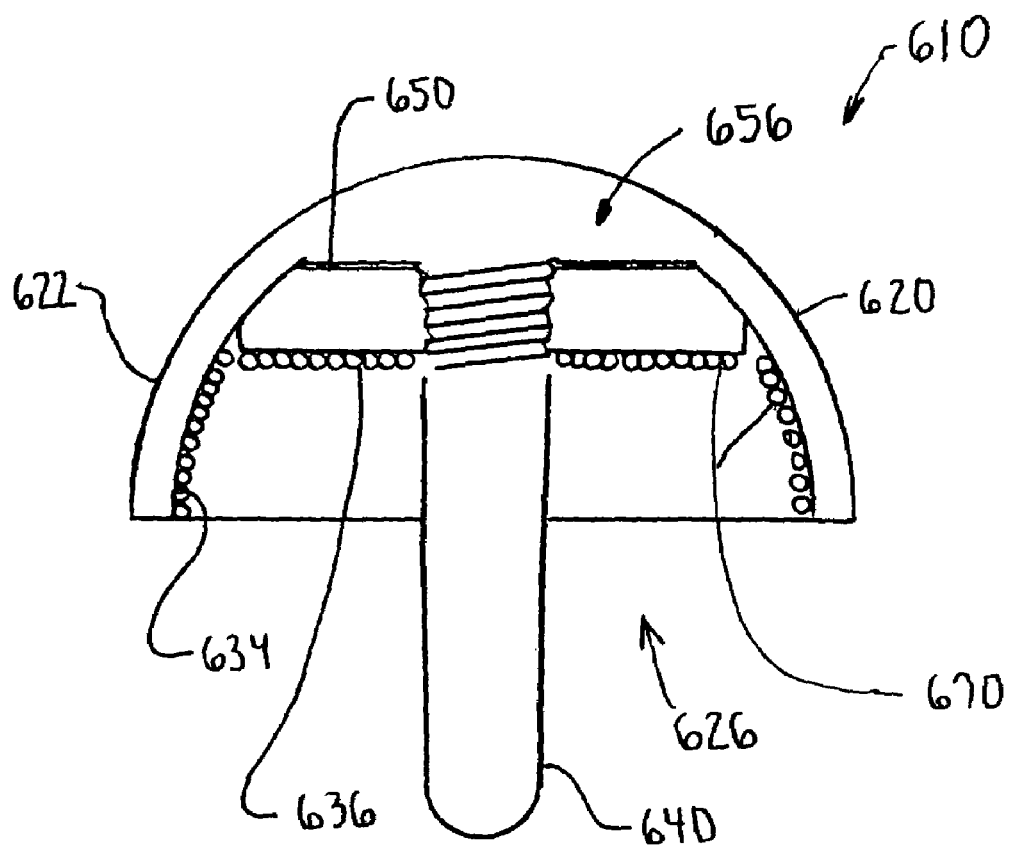
FIG. 15 is a plan view partially in cross section of another embodiment of a surface replacement prosthesis with a screwed-on spacer with a portion of the prosthesis having porous coating for which the gauge of the present invention may be utilized to determine the appropriate size of the spacer.

Referring now to FIG. 15, another embodiment of the present invention is shown as prosthesis 610. Prosthesis 610 is similar to the prosthesis 210 of FIG. 11. Prosthesis 610 includes a body 620 similar to the body 220 of FIG. 11 and includes an articulating surface 622 and opposed arcuate support surface 634. The body 620 includes a stem 640 similar to the stem 240 of FIG. 11. The prosthesis 610 further includes a spacer 650 similar to the spacer 250 of FIG. 11. The spacer 650 includes a planar support surface 636, which together with the arcuate support surface 634 serve to form support surface 626 for supporting the prosthesis 610 against the humerus. The prosthesis 610 further includes a connector 656 similar to the connector 256 of the prosthesis 210 of FIG. 11.

Unlike the prosthesis 210, the prosthesis 610 includes a porous coating 670 located on the planar support surface 636 and the arcuate support surface 634. The porous coating 670 serves to provide additional surface for promoting bony ingrowth into the prosthesis 610 for improved fixation of the prosthesis 610 to the bone contour 12.

Any suitable commercially available porous coating may be suitable for the coating 670. For example, the coating may be in the form of POROCOAT®, a product of the assignee of the instant application. More information regarding the coating may be available by referring to U.S. Pat. No. 3,855,638 to Pilliar, incorporated herein by reference in its entirety.

Figure 16:
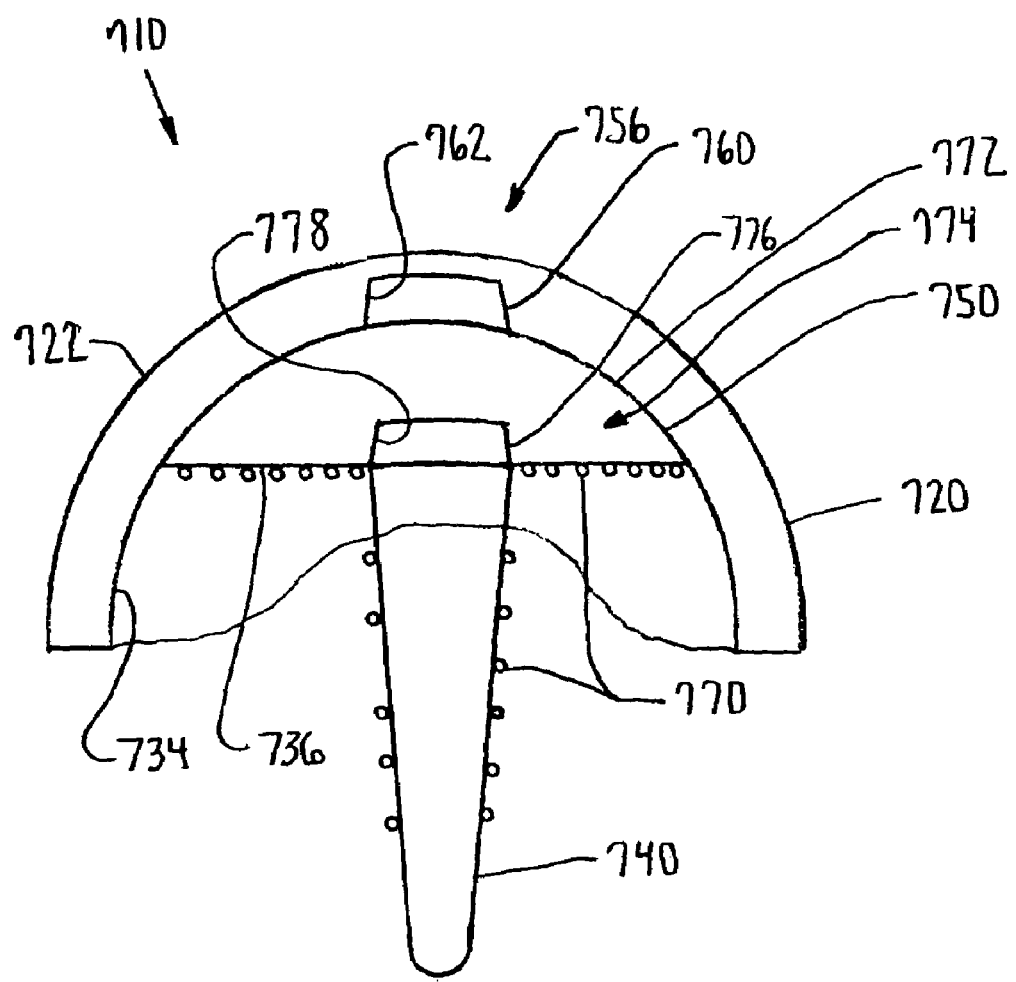
FIG. 16 is a plan view partially in cross section of another embodiment of a surface replacement prosthesis with a three-piece cup, spacer and stem assembly with porous coating for which the gauge of the present invention may be utilized to determine the appropriate size of the spacer.

Referring now to FIG. 16, an alternate prosthesis for use with the gauge of the present invention is shown as prosthesis 710. Prosthesis 710 is a three-part prosthesis including a body 720. The body 720 includes a hemispherical outer articulating surface 722 and a concave internal arcuate support surface 734. The prosthesis 710 further includes a plug 750. The plug 750 includes a planar support surface 736 and an opposed spherical outer surface 772 which mates with the arcuate support surface 734 of the body 720.

The plug 750 may be secured to the body 720 by any suitable method. For example, as shown in FIG. 16, a first connector 756 in the form a taper connection is shown. The first connector 756 includes an exterior taper 760 extending from the plug 750, which mates with an internal taper 762 in the body 720. The prosthesis 710 further includes a generally cylindrical tapered stem 740, which is secured to the plug 750 by a second connector 774.

The stem 740 may be secured to the plug 750 by, for example, the second connector 774. The second connector 774 may have any suitable configuration and may, as shown in FIG. 16, be in the form of an external taper 776 located on the stem 740, which cooperates with an internal taper 778 formed in the plug 750.

As shown in FIG. 16, the prosthesis 710 may further include a coating 770 in the form of, for example, a porous coating, for example, POROCOAT® to encourage ingrowth to assist in the securing of the prosthesis 710 to the bone contour 12. The coating 770 may be secured to the stem 740, as well as to the arcuate support surface 734, as well as the planar support surface 736.

Figure 17:
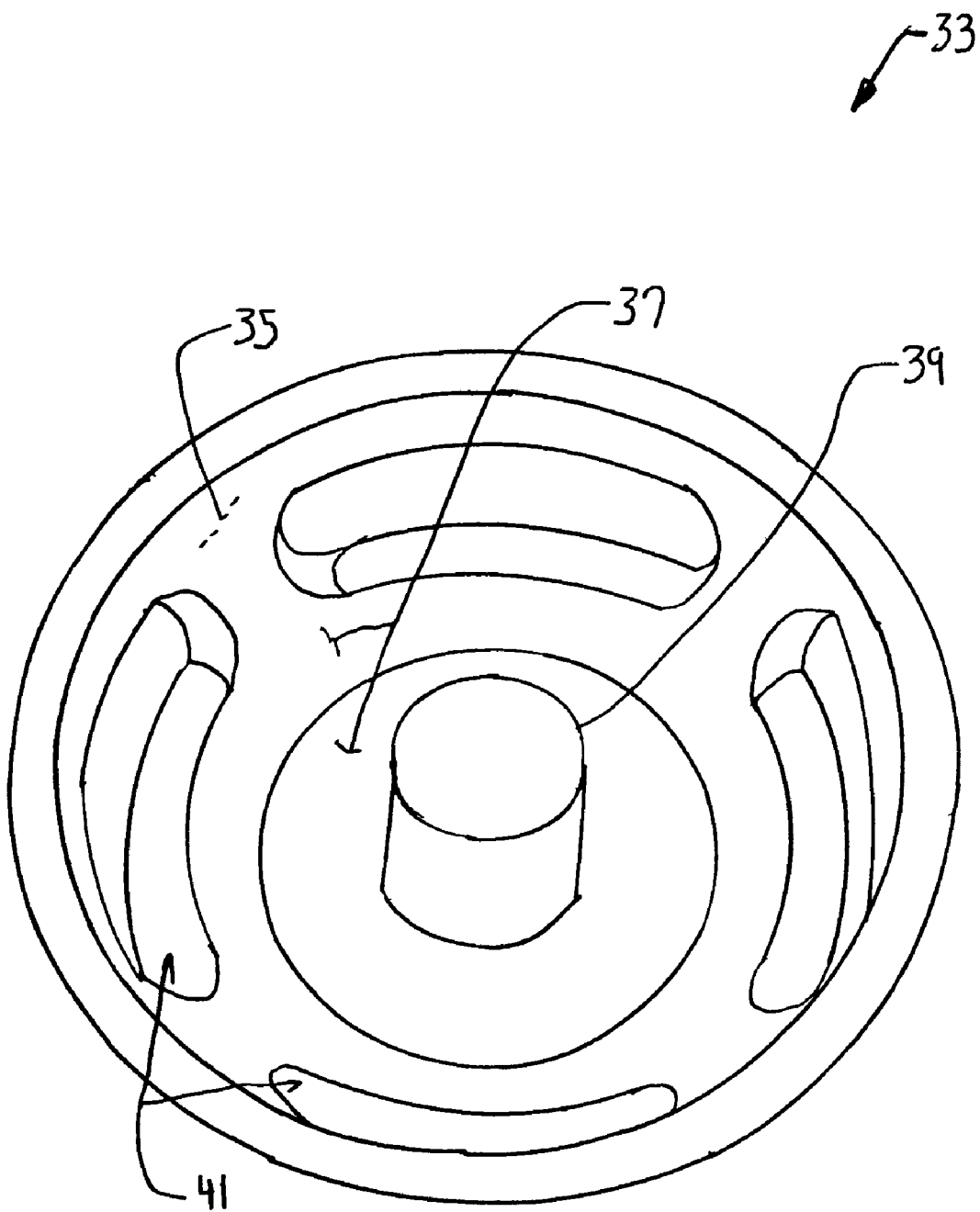
FIG. 17 is a perspective view of a trial for use with the surface replacement prosthesis for which the gauge of the present invention may be utilized to determine the appropriate size of the spacer.

Referring now to FIG. 17, a trial 33 for use with the gauge and surgical method of the present invention is shown. A trial 33 is utilized during shoulder arthroplasty to verify the proper selection of the prosthetic member by implanting the trial 33 into the humeral head and performing trial reductions on the arm to verify the selection of the particularly sized trial and corresponding prosthesis. Just as the gauge 10 of FIG. 1 may be utilized to select the proper dimensions for machining the humeral head of the humerus, as well as for selecting the appropriate prosthetic member to be used, the gauge 10 of FIG. 1 may be utilized to select the proper trial for a particular arthroplasty surgery.

The trial 33 may be removed and replaced with the corresponding prosthesis. The trial 33 may be reused after sterilization. The trial 33 may therefore be made of any suitable durable material and may, for example, be made of a durable plastic that may be sterilized by standard sterilization methods, such as an autoclave.

The trial 33 mimics the size and shape of the prosthesis. The trial 33 therefore includes an articulating surface 35 and an opposed support surface 37. The trial 33 further includes a stem 39 extending outwardly from the support surface 37. As shown in FIG. 17, the trial 33 may also include a plurality of spaced-apart openings 41 to assist in the removal of the trial 33.

Figure 18:
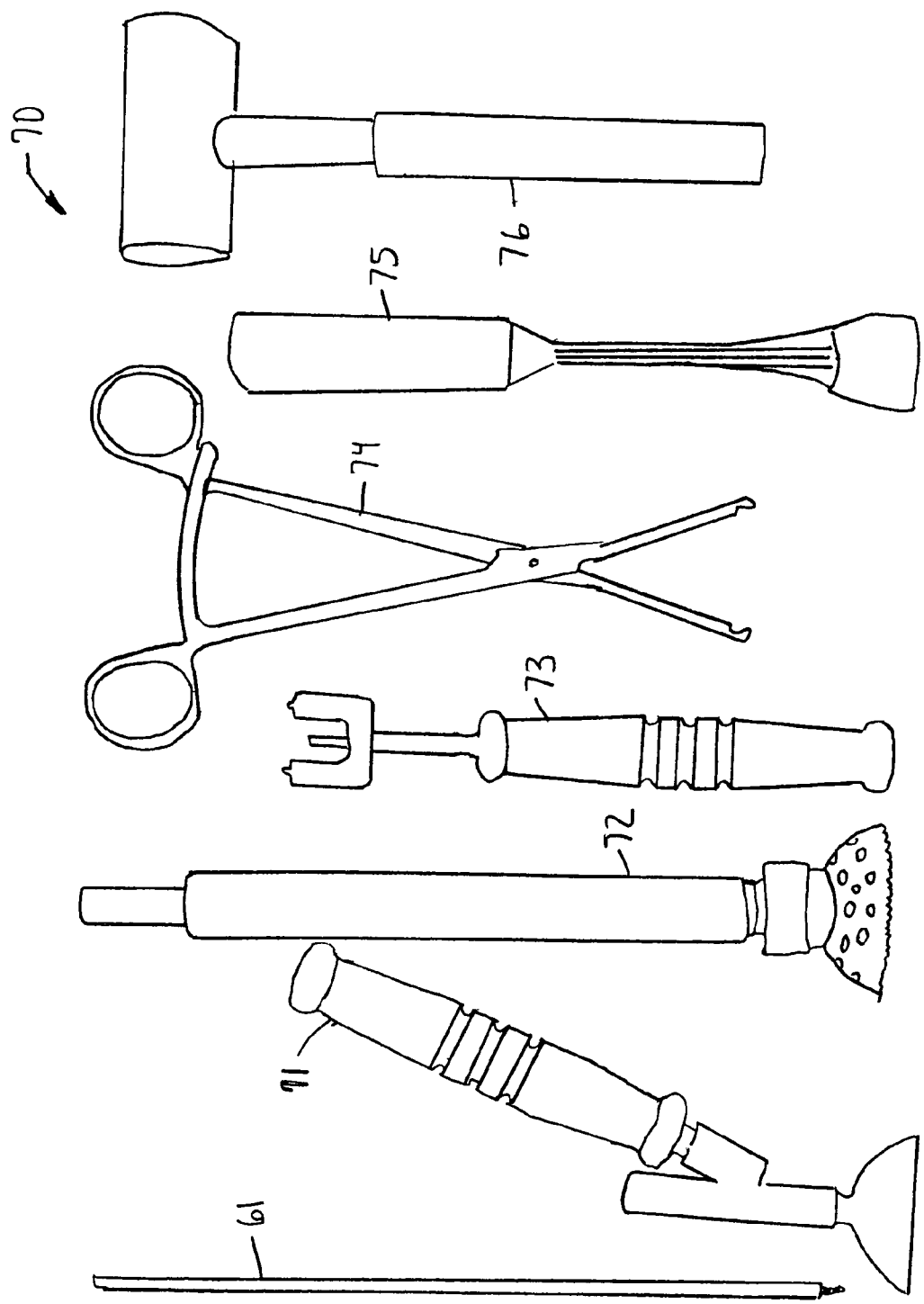
FIG. 18 is a plan view of a set of surgical instruments that may be used in performing shoulder arthroplasty according to a further embodiment of the present invention.

Referring now to FIG. 18, a kit 70 for use when performing an arthroplasty to implant the prosthesis of the present invention. The kit 70 includes a guide pin 61, a guide pin alignment tool 71 for assisting in aligning the guide pin and positioning it into the humerus. The instrument kit 70 also includes a cutting tool assembly 72 for preparing the humeral head. The instrument kit 70 further includes a cutting tool assembly wrench 73 for assembling and disassembling the cutting tool from the cutting tool assembly 72. The instrument kit 70 also includes forceps 74 for securely gripping items. The instrument kit 70 also includes a humeral head impactor 75 which may be used with surgical mallet 76 that drives the implant into its final seat.

It should be appreciated that the cutting tool assembly 72 of the kit 70 of FIG. 18 may be a generally hemispherical grater type reamer. Such a grater type reamer provides for a generally hemispherical shape on the humeral head.

Referring again to FIGS. 5 through 7, the humeral head may have a shape other than a hemispherical shape and may include a planar surface as well as a central bore which may be counterbored. It should be appreciated that the planar surface may be provided by a mill end cutter, reamer or saw and it should be appreciated that the counter bore center opening may be provided by a two-step type reamer or by two separate reamers.

Figure 19:
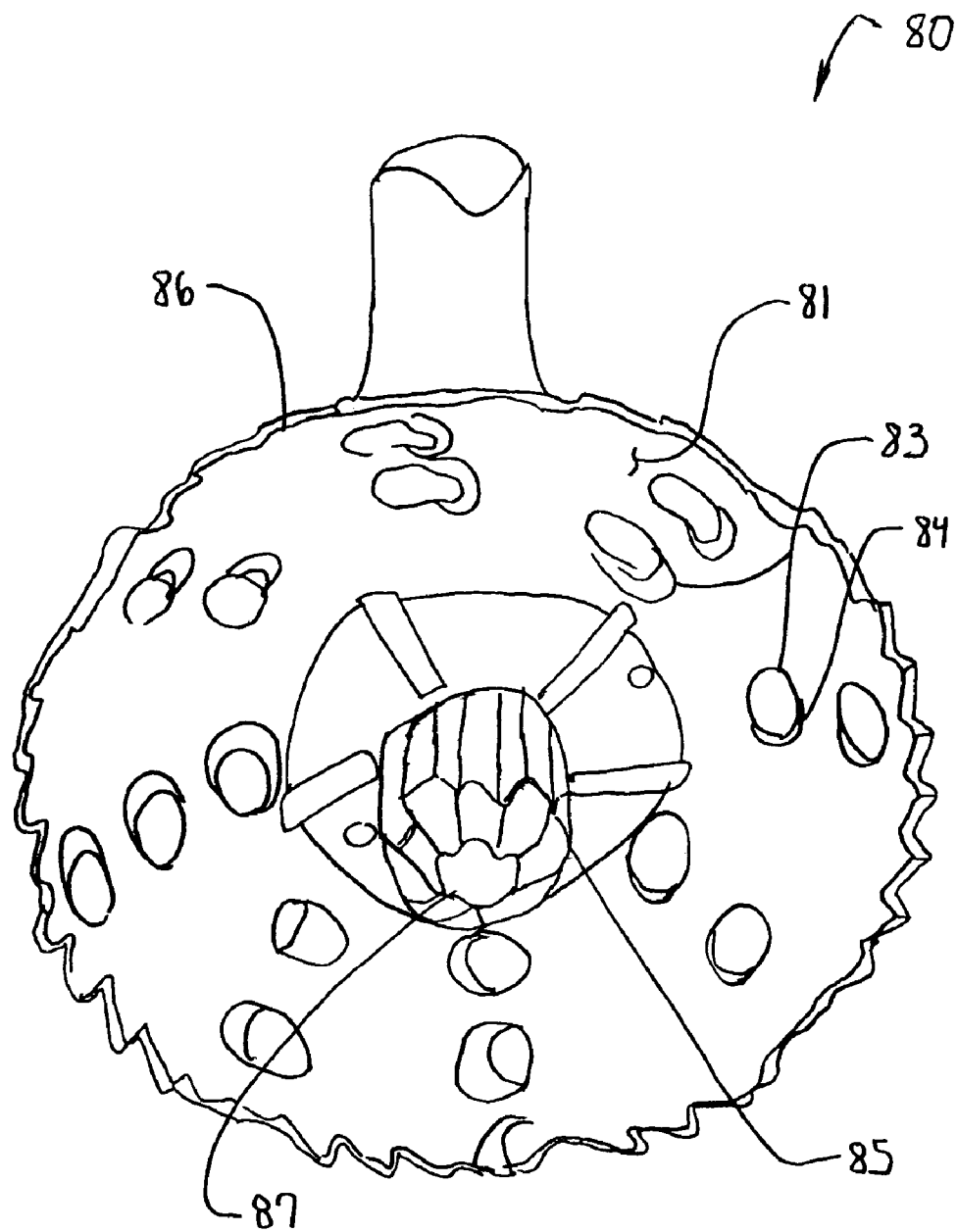
FIG. 19 is a perspective view of a reamer that may be used to prepare the humerus for the surface replacement prosthesis for which the gauge of the present invention may be utilized to determine the appropriate size of the spacer.

Referring now to FIG. 19, the humeral head configuration found in FIGS. 6 and 7, may be formed in one step by utilizing the cutting tool assembly 72 of FIG. 18 with a combination cutting tool reamer 80 as shown in FIG. 19. Applicants have found that a cutting tool in the form of, for example, a reamer 80 may be provided which simultaneously provides the hemispherical shape, the central opening for the stem of the prosthesis, a counter bore, as well as a planar surface.

This cutting tool 80 includes a hemispherical body 81. The hemispherical body 81 is hollow, including a plurality of openings 83 having cutting edges 84 on the edge of the openings 84 for removing the material necessary to form the hemispherical shape on the humerus. The cutting tool 80 also includes a cylindrical reamer 85 for preparing the humerus for receiving a stem prosthesis. The cutting tool 80 may also include a series of circumferential saw teeth 86 located on the outer periphery of the body 81. Further, the cutting tool or reamer 80 may include a central opening 87 for receiving a guide pin to stabilize the reamer during cutting and assure its proper position.

Figure 20:
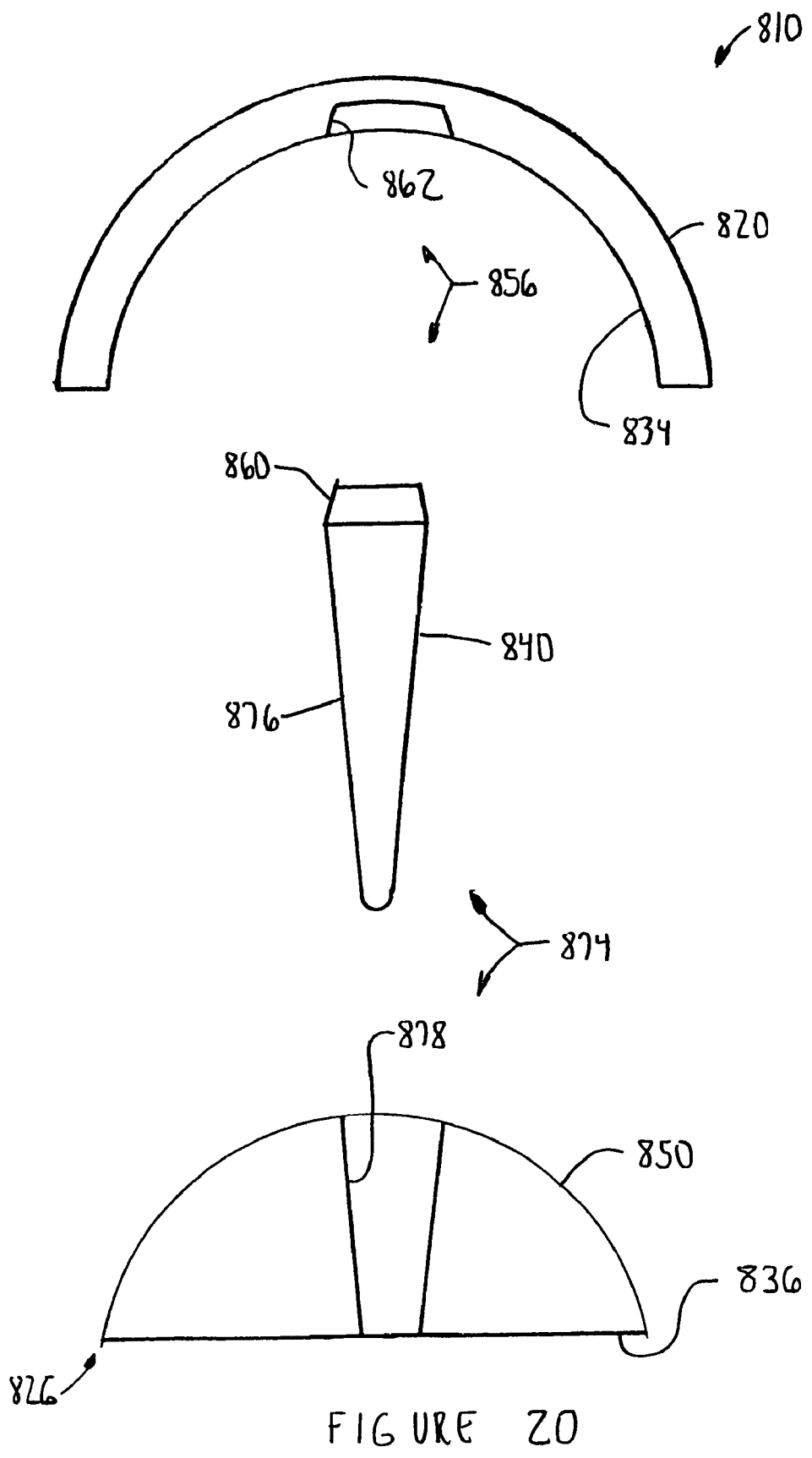
FIG. 20 is an exploded plan view partially in cross section of another embodiment of a surface replacement prosthesis with a three-piece cup, spacer and stem for which the gauge of the present invention may be utilized to determine the appropriate size of the spacer.

Referring now to FIG. 20, an alternate prosthesis for use with the gauge of the present invention is shown as prosthesis 810. Prosthesis 810 is similar to prosthesis 710 of FIG. 16 and includes three components, namely a body 820 similar to body 720 of the prosthesis 710 of FIG. 16, a stem 840 similar to the stem 740 of the prosthesis 710 of FIG. 16, and a plug 850.

The plug 850 is similar to the plug 750 of the prosthesis 710 of FIG. 16 except that the plug 850 and the stem 840 are secured to the body 820 in a different fashion from that of the prosthesis 710. While the prosthesis 810 similar to the prosthesis 710 has its components interconnected by means of tapered connections, the tapered connections of the prosthesis 810 are different from those of the prosthesis 710 of FIG. 16.

For example, the prosthesis 810 includes a first connector 856 in the form of a tapered connection. The tapered connection 856 includes an external taper 860 formed on the stem 840 which connects with an internal taper 862 formed on the body 820. The plug 850 is secured to the stem 840 by means of a second tapered connection 874. The second tapered connection 874 includes an external taper 876 formed on the stem 840 which connects with an internal taper 878 formed on the plug 850. The plug 850 includes a support surface 836 that, together with the arcuate surface 834 of the body 820 form support surface 826 of the prosthesis 810 for the securing the prosthesis 810 to the humerus.

Figure 21:
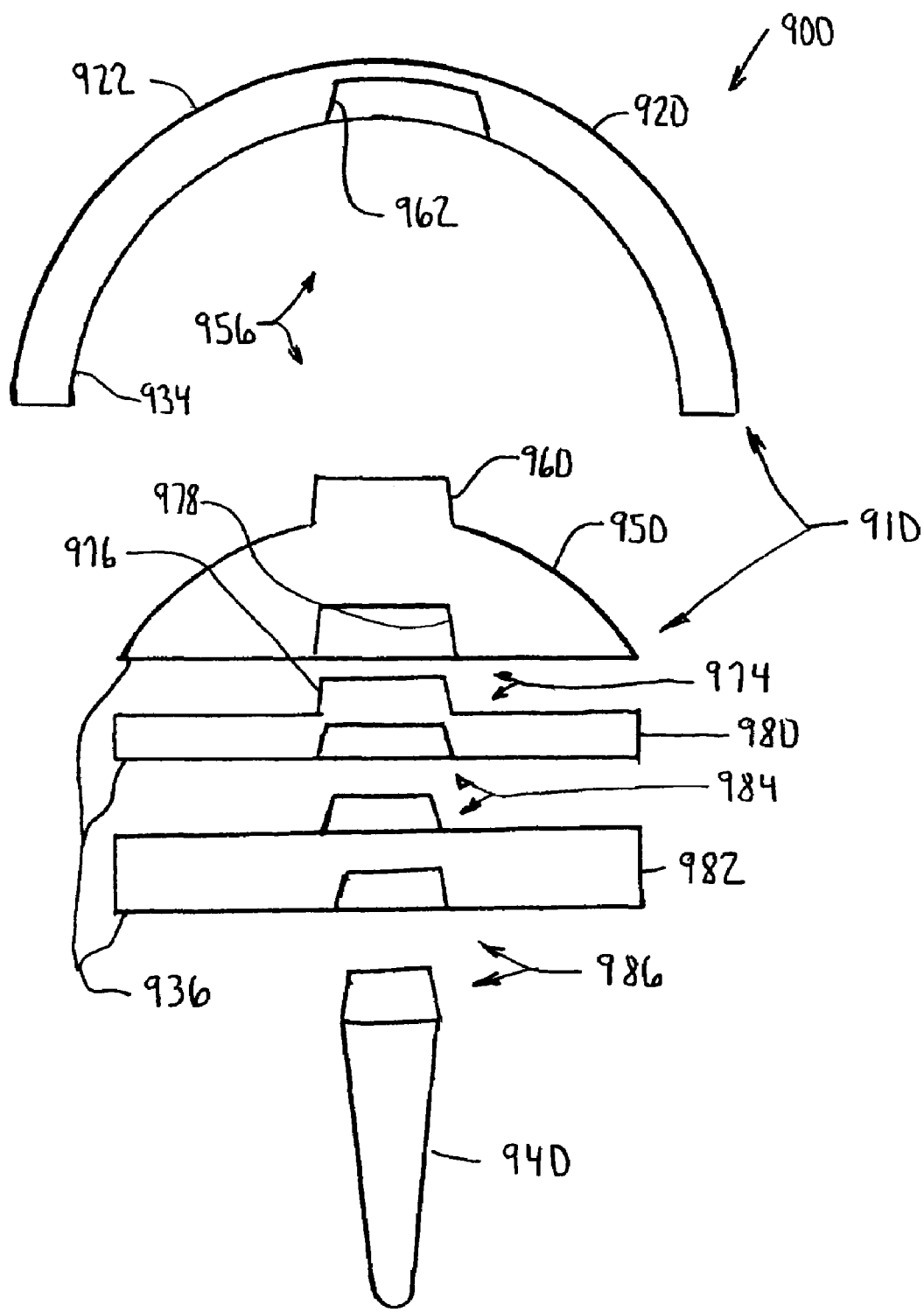
FIG. 21 is an exploded plan view partially in cross section of another embodiment of a surface replacement prosthesis kit with a three-piece cup, a set of two spacers and a stem for which the gauge of the present invention may be utilized to determine the appropriate size of the spacer.

Referring now to FIG. 21, another prosthesis for use with the gauge of the present invention is in the form of a kit and is shown as kit 900. The kit 900 includes a body 920 similar to the body 720 of the prosthesis 710 of FIG. 16. The body 920 includes an articulating surface 922 and an opposed support surface 934. The kit 900 further includes a first spacer in the form of a plug 950. The first spacer 950 is similar to the first spacer or plug 750 of the prosthesis 710 of FIG. 16.

The body 920 and the first spacer 950 combine to form prosthetic member 910. The prosthetic member 910 may further include an optional stem 940 similar to the stem 740 of FIG. 16. The kit 910 in addition to the first spacer 950 includes a second spacer 980.

The second spacer 980 may selectively be included or excluded from the prosthetic member 910 such that planar support surface 936 may be located for example on the first spacer 950 or alternatively on the second spacer 980. The kit 900 may optionally further include a third spacer 982 or additional spacers not shown. When the kit 900 includes the body 920, the first spacer 950 and the second spacer 980, the kit 900 may be utilized by selectively picking the inclusion or non-inclusion of the second spacer 980, thereby providing for a variation in the location of the support surface 936.

The kit 900 permits the use of a prosthesis with a variety of locations for the support surface 936. The ability to vary the location of the support surface is important when dealing with diseased humerus in which the flattened head may vary from patient to patient, and the corresponding required amount of resection may vary for a given geometry of the humerus.

The prosthetic of kit 900 may be built by utilizing the body 920 and the plug 950 as well as a combination of one or the other of the second and third spacers 980 or 982, respectively, or by the use of both spacers 980 and 982. Similarly, the prosthetic member 910 may be performed without the use of either the second spacer 980 or the third spacer 982.

Preferably, and as shown in FIG. 21, the first spacer 950 is secured to the body 920 by use of a first tapered connection 956. The first tapered connection 956 as shown in FIG. 21, includes an external taper 960 formed on the first spacer 950, which mates with an internal taper 962 formed on the body 920. The second spacer 980 may be secured to the plug 950 by the use of a second tapered connection 974.

The second tapered connection 974 may include an external taper 976 formed on the second spacer 980 which mates with an internal taper 978 formed in the first spacer 950. Similarly, the second spacer 980 may be connected to the third spacer 982 by means of a third tapered connection 984. Similarly, the third spacer 982 may be connected to the stem 940 by means of a fourth tapered connection 986.

Preferably, and as shown in FIG. 21, the second tapered connection 974, the third tapered connection 984 and the fourth tapered connection 986 are identical to each other so that the stem 940 may be connected to any of the first spacer 950, second spacer 980 or third spacer 982.

Figure 22:
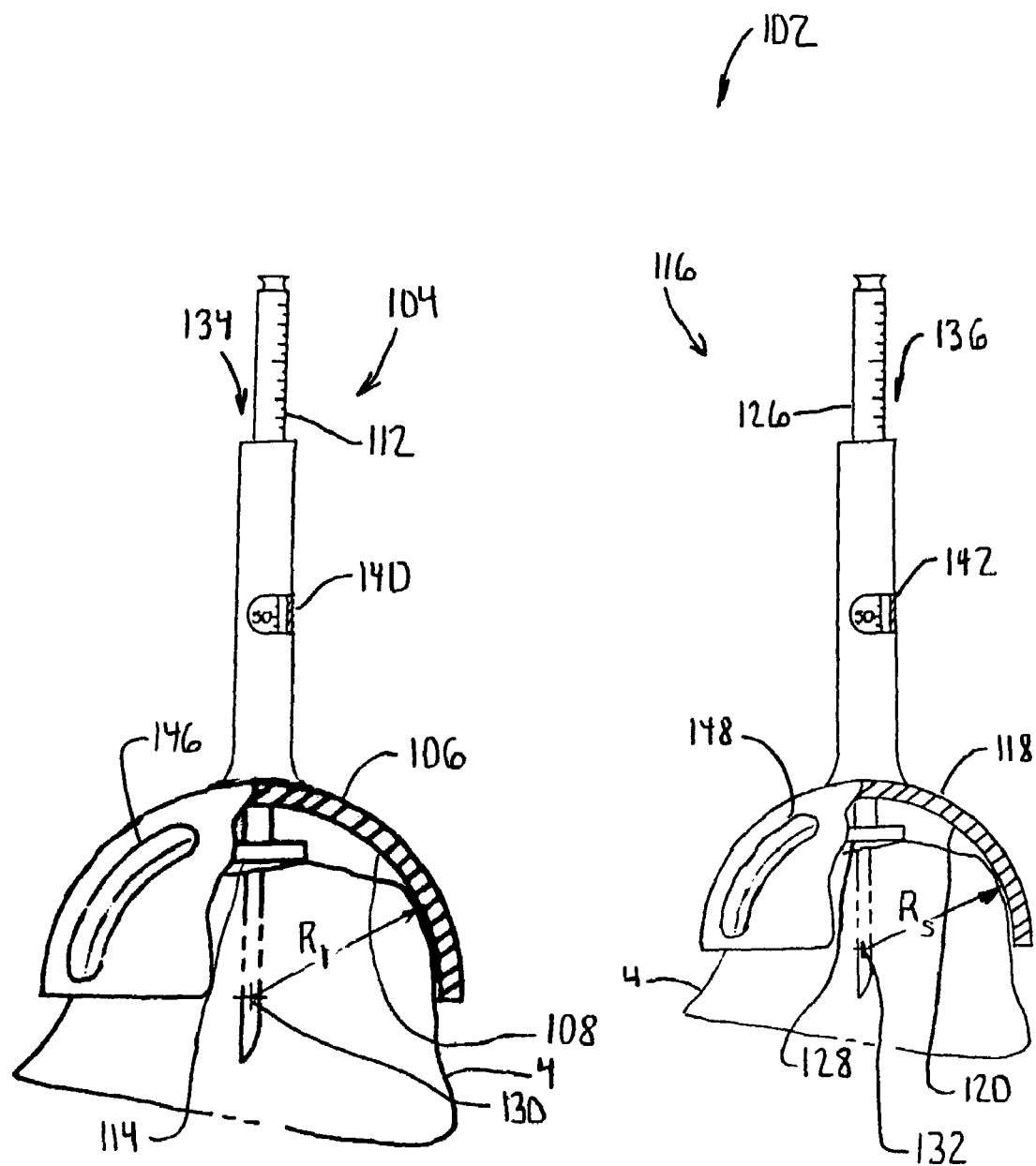
FIG. 22 is a plan view of a kit including a plurality of gauges for use in performing shoulder arthroplasty according to a further embodiment of the present invention.

Referring now to FIG. 22, a kit for use in performing joint arthroplasty on a bone according to the present invention is shown as kit 102. The kit 102 includes a first gauge 104, including a first gauge body 106 having a body contact portion 108 for contact with the bone 4. The first gauge 104 further includes a first gauge probe 112 movably positioned with respect to the body 106. The first gauge probe 112 includes a contact portion 114 for contact with the bone 4. The relative position of the first gauge probe 112 with respect to the first gauge body 106 is indicative of the contour of the bone 4.

The kit 102 further includes a second gauge 116. The second gauge 116 includes a second gauge body 118 having a body contact portion 120 for contact with the bone 4. The second gauge 116 further includes a second gauge probe 126 movably positionable with respect to the second gauge body 118. The second gauge probe 126 includes a probe contact portion 128 for contact with the bone 4. The relative position of the second gauge probe 126 with respect to the second gauge body 118 is indicative of the bone contour of the bone 4. The second gauge 116 has at least one dimension different from that of the first gauge 104.

While the dimensions that may be different from the first gauge 104 to the second gauge 116 may be any dimension, for example, one such dimension represents the body contact portion 108 of the first gauge 104 and the body contact portion 120 of the second gauge 116. It is the contact portions 108 and 120 that are designed to correspond to a particular dimension of a prepared humerus and a particular dimension to a corresponding prosthesis to be implanted.

Thus, for each particular size prepared radius of a humeral head, a particular gauge should be used. For each of those particular gauges that should be used, a corresponding prosthesis should be selected. For example, as shown in FIG. 22, the body contact portion 108 of the first gauge 104 is defined by center point 130 from which radius $R_1$ is used to describe the locus of points defining the body contact portion 108 of the first gauge 104. Similarly, radius $R_s$ extending from center point 132 of the second gauge 116 defines the locus points defining the body contact portion 120 of the second gauge 116. Radius $R_1$ and radius $R_s$ are different and correspond to a particular prepared humeral head and a particular inner periphery of a implantable prosthesis.

As shown in FIG. 22, the first gauge 104 and the second gauge 116 may include longitudinal openings 134 and 136, respectively. The first gauge probe 112 may be in the form of a rod that slidingly fits in the opening 134. Similarly, the second gauge probe 126 may be in the form of a rod that is slidably fitable into the second gauge opening 136.

As shown in FIG. 22, the first gauge 104 may include indicia 140 corresponding to the relative position of the first gauge body 106 to the first gauge probe 112. Similarly, the second gauge 116 may include indicia 142 corresponding to the relative position of the second gauge body 118 to the second gauge probe 126. The first gauge body 106 of the first gauge 104 may include a viewing opening 146 for viewing the bone 4 and similarly, the second gauge 116 may include a viewing opening 148 in the second gauge body 118 for viewing the bone 4.

Figure 23:
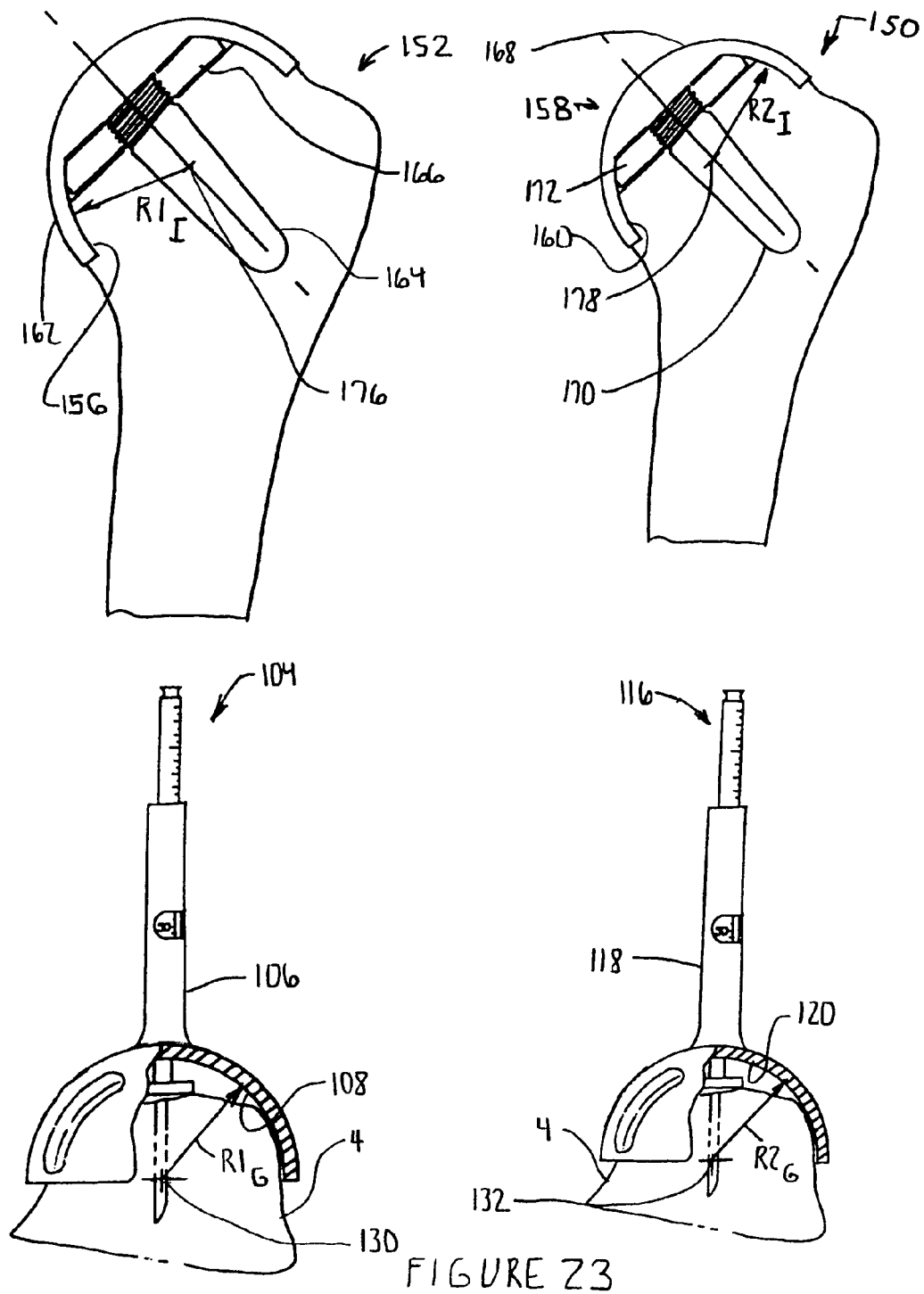
FIG. 23 is a plan view of a kit including a plurality of prostheses and gauges for use in performing shoulder arthroplasty according to a further embodiment of the present invention.

Referring now to FIG. 23, another embodiment of the present invention is shown as kit 150. Kit 150 is similar to kit 102 and includes first gauge 104, as well as, second gauge 116 of FIG. 22. The kit 150, however, further includes a first implant 152, including a first implant surface 156 for contact with the bone. The kit 150 further includes a second implant 158, including a second implant surface 160 for contact with the bone. The second implant 158 has at least one dimension different from the corresponding dimension of the first implant 152.

While the implants 152 and 158 may have any suitable shape and may be unitary or be made from multiple pieces, for example, as shown in FIG. 23, the first implant 152 includes a body 162 and a stem 164 extending from the body 162. The first implant 152 further includes a spacer 166 positioned between the stem 164 and the body 162. Similarly, the second implant 158 includes a body 168 and a stem 170 extending from the body 168. A spacer 172 is positioned between the body 168 and the stem 170.

While the kit 150 includes a pair of implants with the pair having a different or unique dimension and a pair of gauges with the gauges each having a particular unique dimension, an example of different dimension for the gauges and the implants as shown in the kit 150 of FIG. 23 includes, for example, a body contour portion 108 of the body 106 of the gauge 104 having a dimension defined by dimension $R1_G$ extending from center point 132. The dimension $R1_G$ is significantly different than the dimension $R2_G$ of the body contour portion 120 of the second gauge 116.

Further, as shown in FIG. 23, the first implant 152 has a first implant surface 156 defined by radius $R1_I$ extending from center point 176. The second implant 158 includes the second implant surface 160 defined by radius $R2_I$ extending from center point 178. The dimension $R1_I$ of the first implant surface 156 is significantly different from the $R2_I$ of the second implant surface 160. As shown in FIG. 23, the body contact portion 108 of the first gauge 104 corresponds to the first implant surface 156 of the first implant 152. Similarly, the body contact portion 120 of the second gauge 116 corresponds to the second implant surface 160 of the second implant 158.

Therefore, the first gauge 104 is utilized with the first implant 152 and correspondingly, the second gauge 116 is used with the second implant 158. In other words, the radius $R1_G$ of the first gauge 104 is identical to the radius $R1_I$ of the first implant 152. Similarly, the radius $R2_G$ of the second gauge 116 is identical to the radius $R2_I$ of the second implant 158.

Figure 24:
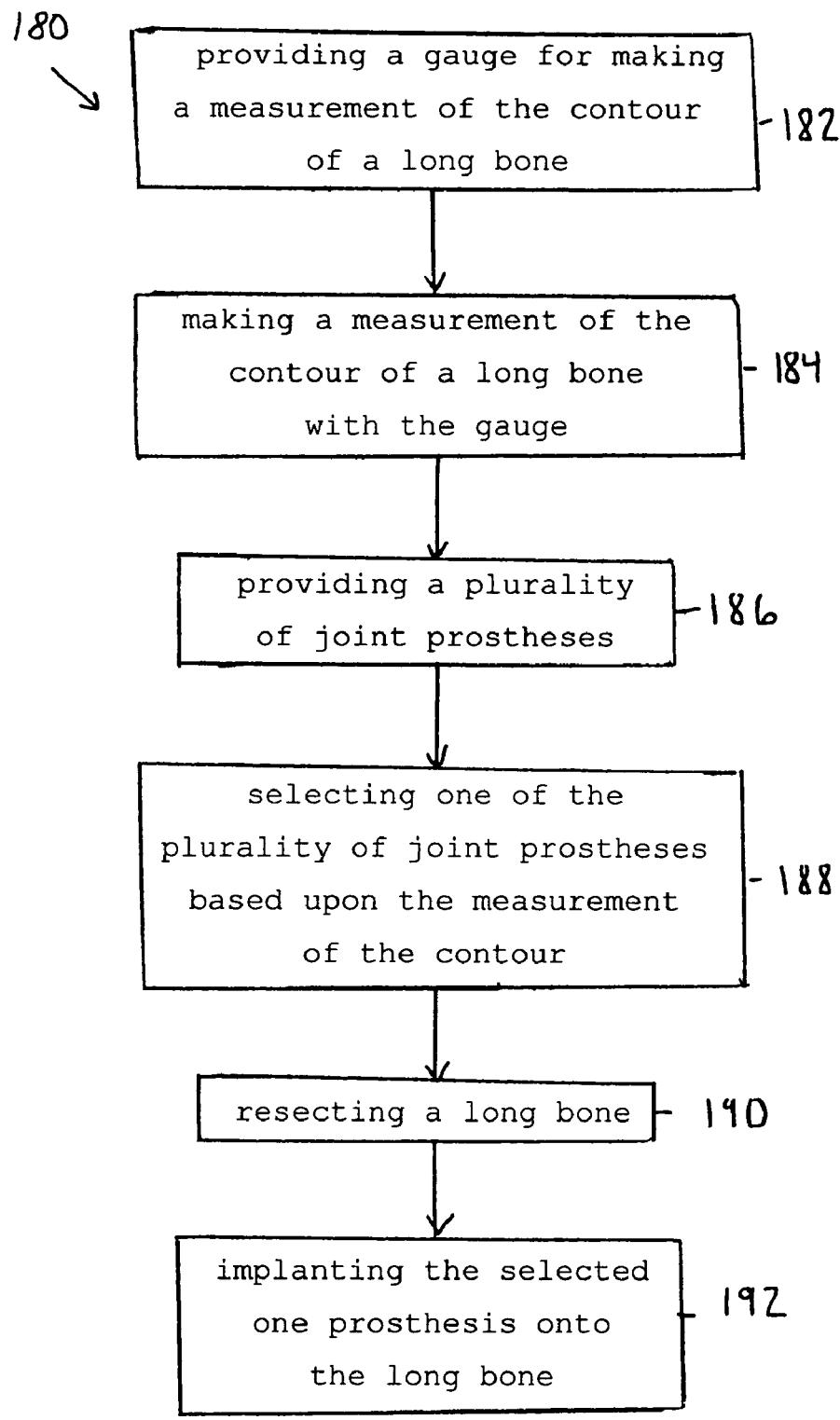
FIG. 24 is a process flow chart for a method of performing shoulder arthroplasty according to another embodiment of the present invention.

Referring now to FIG. 24, a method 180 for performing arthroplasty is shown. The method includes a first step 182 of providing a gauge for making a measurement of the contour of a long bone. The method further includes a second step 184 of making a measurement of the contour of a long bone with a gauge. The method 180 further includes a third step 186 providing a plurality of joint prostheses. The method 180 further includes a fourth step 188 of selecting one of the plurality of joint prostheses based upon the measurement of the contour and a fifth step 190 of resecting a long bone. The method 180 further includes a sixth step 192 of implanting the selected one prosthesis onto the long bone.

Figure 25:
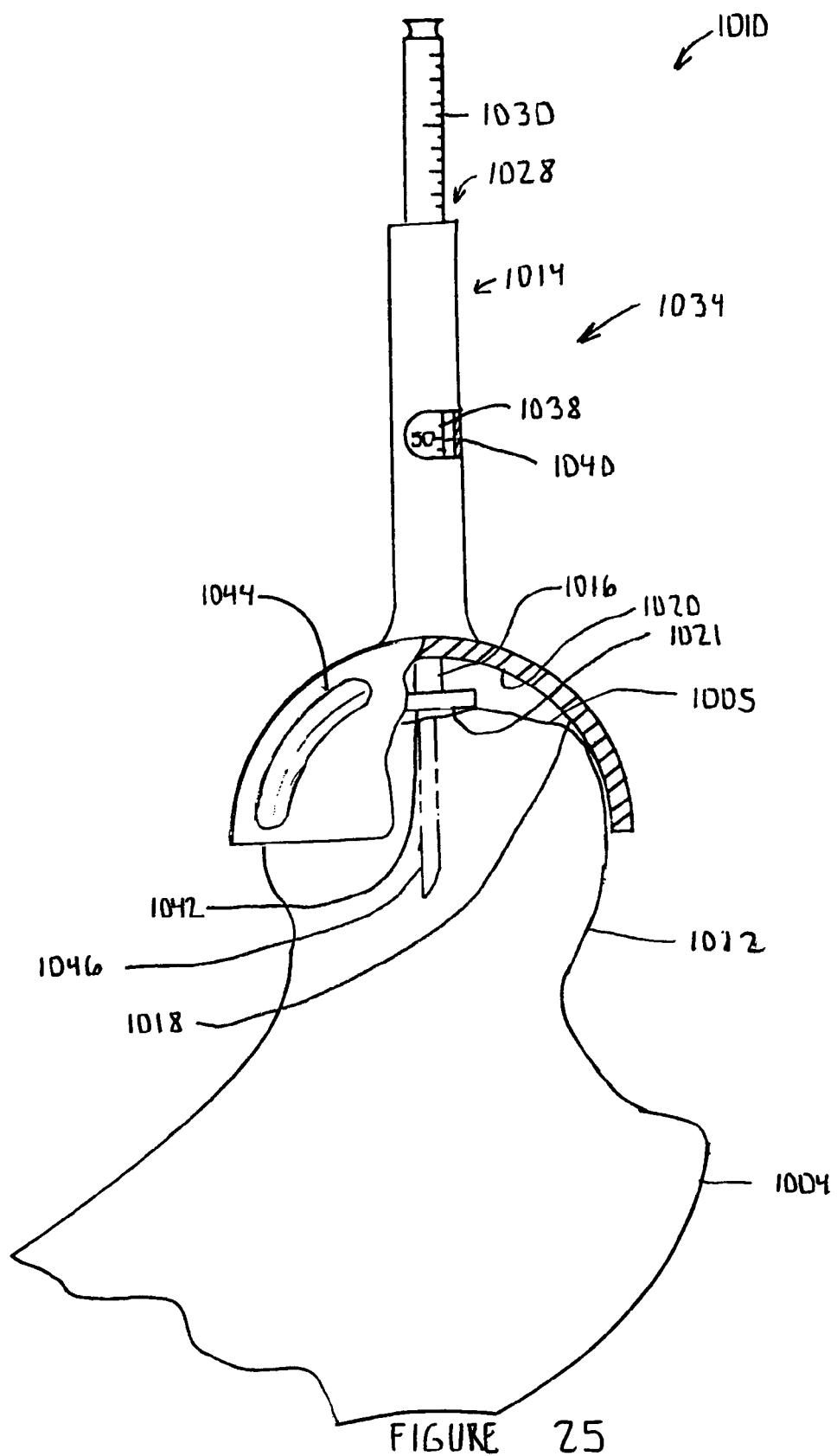
FIG. 25 is a plan view partially in cross section of a gauge for use with a femur according to another embodiment of the present invention.

According to the present invention and referring now to FIG. 25, another embodiment of the present invention is shown as gauge 1010. The gauge 1010 is used for measuring femur contour 1012 of the femur 1004 for use in hip arthroplasty. The gauge 1010 is similar to the gauge 10 of FIG. 1 except the gauge 1010 is designed for use with the femoral head. The gauge 1010 includes a body 1014 and a probe 1016. The body 1014 has a body contact portion 1018 of the body 1014 for contact with the femur 1004. The probe 1016 is movably positional with respect to the body 1014. The probe 1016 includes a contact portion 1021 of the probe 1016 for contact with the femur 1004. The relative position of the probe 1016 with respect to the body 1014 is indicative of the femur contour 1012 of the femur 1004.

The gauge 1010 may, as shown in FIG. 25, be such that at least a portion of the body contact portion 1018 for contact with the femur 1004 includes a contoured portion 1020 with a periphery similar to the internal periphery of the prosthesis to be implanted.

The gauge 1010 of FIG. 25 may, for example, provide that at least a portion of the body 1014 includes a concave surface. As shown in FIG. 25, the internal periphery 1020 may be concave. In fact, as shown in FIG. 25, the internal periphery 1020 may be hemispherical. While the probe 1016 may be movably positioned with respect to the body 1014 in any suitable fashion, as shown in FIG. 25, the body 1014 defines a longitudinal opening 1028 therein. As shown in FIG. 25, the probe 1016 may be slidably fitted into the opening 1028.

As shown in FIG. 25, the probe 1016 may include a generally cylindrical portion 1030. The longitudinal opening 1028 may be generally cylindrical.

The gauge of the present invention may, as shown in FIG. 25, include indicia 1034 located on the body 1014 or the probe 1016. It should be appreciated that the indicia 1034 may be located on both the probe 1016 and the body 1014. The indicia 1034 correspond to the relative position of the probe 1016 with respect to the body 1014. The indicia 1034 may have any suitable form and may, for example, include marks 1038 or characters 1040 in the form of, for example, numerals or letters. The marks 1038 and the characters 1040 may be located on either the body 1014 or the probe 1016.

The alignment of a solitary mark 1038 on the body with the corresponding mark 1038 on the probe corresponds to the relative position of the femur contact surface 1042 of the contact portion 1021 of the probe 1016. As shown in FIG. 25, the probe 1016 adjacent the femur contact surface 1042 may be substantially wider than cylindrical portion 1030 of the probe 1016 in order to obtain a more representative indication of the femur contour 1012.

As shown in FIG. 25, the body 1014 of the gauge 1010 may include a viewing opening 1044 for visually sighting the condition of the femur contour 1012, while positioning the gauge 1010 with respect to the femur contour 1012. The viewing opening 1044 may have any shape but may, as shown in FIG. 25, be generally elongate and arcuate corresponding to the femur contour 1012.

Referring again to FIG. 25, the gauge 1010 may provide an additional function to that already mentioned by being able to be used to assist in preparing a locating hole 1046 in the head 1005 of the femur 1004. The locating hole 1046 may be used to guide tools used to prepare the head 1005 of the femur 1004 for an appropriate prosthesis. When utilizing the gauge 1010 to prepare the locating hole 1046, the body 1014 of the gauge 1010 is brought in a position relative to the head 1005 of the femur 1004 by sight as it is located along the femur contour 1012. Using the viewing window 1044, as well as, the cylindrical portion 1022 of the body 1014 as guides to determine the proper orientation of the locating hole 1046. A drill in the form of, for example, a standard spiral point drill having a size compatible for a sliding fit with opening 1028 may be inserted through opening 1028 and used to form the locating hole 1046 after the probe 1016 has been removed from the body 1014 of the gauge 1010.

Although the present invention and its advantages have been described in detail, it should be understood that various changes, substitutions, and alterations can be made therein without departing from the spirit and scope of the present invention as defined by the appended claims.

We claim:

1. A gauge for measuring bone contour of a bone for use in joint arthroplasty, said gauge comprising:
    a body including a body contact portion thereof for contact with the bone, said body contact portion comprises a hemispherical concave surface wherein the hemispherical concave surface is configured to contact bone during use of the gauge, wherein said body further includes a hemispherical concave surface located at the apex of the generally cylindrical portion; and a probe, movably positionable with respect to said body and sized and shaped to fit within the generally cylindrical portion of the body, said probe including a probe contact portion such that when the probe is received within the generally cylindrical portion, the probe contact portion contacts an outer contour of the bone, the relative position of said probe with respect to said body being indicative of a contour of the bone; wherein the relative position of the probe with respect to the body is used to determine a particular size of a prosthesis appropriate for the measured contour of the bone.

2. The gauge of claim 1, wherein at least a portion of the contact portion of said body comprises a body internal periphery similar to a prosthesis internal periphery of a prosthesis to be implanted.

3. The gauge of claim 1, wherein at least one of said body and said probe includes indicia thereon corresponding to the relative position of said probe with respect to said body.

4. The gauge of claim 1, wherein said body defines an opening for viewing the bone.

5. The gauge of claim 1:
wherein said probe defines a longitudinal opening there through; and
further comprising a rod slidably fitted to the longitudinal opening.

6. The gauge of claim 1:
wherein the bone is one of a femur and a humerus; and
wherein the joint is one of a hip and a shoulder.

7. A kit for use in selecting one of a plurality of joint implants for use in joint arthroplasty on a bone, said kit comprising:
a first gauge, said first gauge including a first gauge body having a body contact portion thereof for contact with the bone, said body contact portion comprises a concave surface, wherein said first gauge body includes a generally cylindrical portion located at the apex of the concave surface, and a first gauge probe, movably positional with respect to the body and sized and shaped to fit within the generally cylindrical portion of the first gauge body, the first gauge probe including a probe contact portion thereof for contact with an outer contour of the bone, the relative position of the first gauge probe with respect to the first gauge body being indicative of the bone contour of the bone; wherein the relative position of the probe with respect to the body is used to determine a particular size of a prosthesis appropriate for the measured contour of the bone; and a second gauge, said second gauge including a second gauge body having a body contact portion thereof for contact with the bone, said body contact portion comprises a concave surface, wherein said body includes a generally cylindrical portion located at the apex of the concave surface, and a second gauge probe, movably positional with respect to the second gauge body and sized and shaped to fit within the generally cylindrical portion of the second gauge body, the second gauge probe including a probe contact portion thereof for contact with an outer contour of the bone, the relative position of the second gauge probe with respect to the second gauge body being indicative of the bone contour of the bone; wherein the relative position of the probe with respect to the body is used to determine a particular size of a prosthesis appropriate for the measured contour of the bone.

8. The kit of claim 7, wherein at least one of the body contact portion of the first gauge body and the body contact portion of the second gauge body comprises a portion thereof with a contour similar to the one of the plurality of joint implants to be implanted.

9. The kit of claim 7, wherein at least one of the body contact portion of the first gauge body and the body contact portion of the second gauge body includes a concave surface thereof for contact with the bone.

10. The kit of claim 9, wherein the concave surface is hemispherical.

11. The kit of claim 10, wherein at least one of said first gauge and said second gauge includes indicia thereon corresponding to the relative position of at least one of the first gauge body with respect to the first gauge probe and the second gauge body with respect to the second gauge probe.

12. The kit of claim 7, wherein at least one of said first gauge and said second gauge defines an opening for viewing the bone.

13. The kit of claim 7:
wherein at least one of said first gauge and said second gauge defines a longitudinal opening there through; and
wherein said probe comprises a rod slidably fitted to the longitudinal opening.

14. The kit of claim 7:
wherein the bone is one of a femur and a humerus; and
wherein the joint is one of a hip and a shoulder.

* * * * *